US012766009B2

(12) United States Patent
Emstad

(10) Patent No.: US 12,766,009 B2
(45) Date of Patent: Oct. 20, 2026

(54) IMPLANT INSERTER ASSEMBLY

(71) Applicant: Elevation Spine, Inc., Monterey, CA (US)

(72) Inventor: Erik Emstad, Laurel Springs, NC (US)

(73) Assignee: Elevation Spine, Inc., Monterey, CA (US)

( * ) Notice: Subject to any disclaimer, the term of this patent is extended or adjusted under 35 U.S.C. 154(b) by 0 days.

(21) Appl. No.: 18/814,480

(22) Filed: Aug. 24, 2024

(65) Prior Publication Data

US 2025/0120824 A1 Apr. 17, 2025

Related U.S. Application Data

(60) Provisional application No. 63/544,538, filed on Oct. 17, 2023.

(51) Int. Cl.
*A61F 2/46* (2006.01)

(52) U.S. Cl.
CPC .................................. *A61F 2/4611* (2013.01)

(58) Field of Classification Search
CPC ............ A61F 2/4455; A61F 2002/4622; A61F 2/447; A61F 2/46; A61F 2/4611
See application file for complete search history.

(56) References Cited

U.S. PATENT DOCUMENTS 7,169,153 B2 * 1/2007 Keller .................. A61F 2/4611
606/99
7,625,379 B2 12/2009 Puno et al.
7,625,380 B2 12/2009 Drewry et al.
8,114,088 B2 2/2012 Miller
8,267,939 B2 9/2012 Cipoletti et al.
8,486,083 B2 7/2013 Puno et al.
8,562,621 B2 10/2013 Mignucci et al.
8,864,830 B2 10/2014 Malandain
8,968,325 B2 3/2015 Mignucci et al.
9,937,055 B1 4/2018 Bernhardt, Jr. et al.
9,937,061 B2 4/2018 Davenport et al.
10,500,063 B2 12/2019 Skolnick et al.
10,603,186 B2 3/2020 Bernhardt, Jr. et al.
10,806,598 B2 10/2020 Davenport et al.
10,888,435 B2 1/2021 Adamo et al.
11,452,618 B2 9/2022 Harding et al.
(Continued)

*Primary Examiner* — Eduardo C Robert
*Assistant Examiner* — Holly Joanna Lane
(74) *Attorney, Agent, or Firm* — Schwegman, Lundberg & Woessner, P.A.

(57) ABSTRACT

A system for inserting an implant into an intervertebral space may include an implant inserter having first and second arms, and a first retention member. The first and second arms may be moveable between a locked configuration, in which the first and second arms are spaced apart such that the arms are locked in place relative to the implant, and a compressed configuration, in which the first and second arms are less spaced apart such that the arms are withdrawable from the implant. The retention member may be moveable between a locked position, in which the first retention member blocks relative motion of the first and second arms from the locked configuration to the compressed configuration, and an unlocked position, in which the first retention member does not block relative motion of the first and second arms from the locked configuration to the compressed configuration.

27 Claims, 23 Drawing Sheets

(56) References Cited

U.S. PATENT DOCUMENTS

| | | | | |
|---|---|---|---|---|
| 11,744,717 | B2 | 9/2023 | Kleiner et al. | |
| 11,766,342 | B2 | 9/2023 | Murillo et al. | |
| 2004/0106927 | A1* | 6/2004 | Ruffner | A61B 17/1671 606/85 |
| 2014/0156009 | A1* | 6/2014 | Armstrong | A61F 2/30771 623/17.16 |
| 2019/0000638 | A1* | 1/2019 | Gilbride | A61F 2/447 |
| 2020/0246182 | A1* | 8/2020 | Ivri | A61M 35/003 |
| 2020/0345515 | A1* | 11/2020 | Arramon | A61F 2/4611 |
| 2021/0068973 | A1* | 3/2021 | McLuen | A61F 2/4455 |
| 2022/0133497 | A1* | 5/2022 | Dewey | A61F 2/4455 623/17.16 |

* cited by examiner

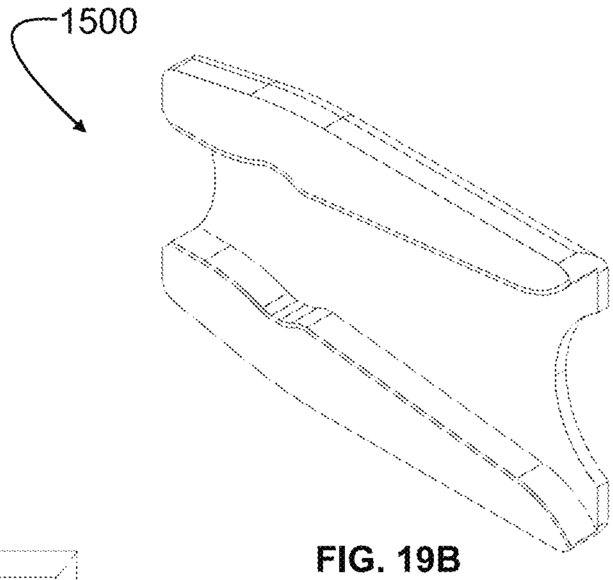
FIG. 19B
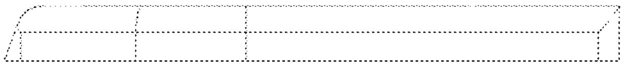
FIG. 19A
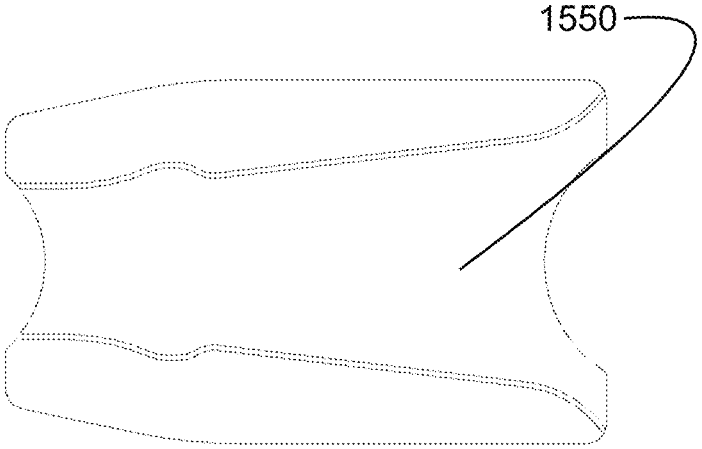
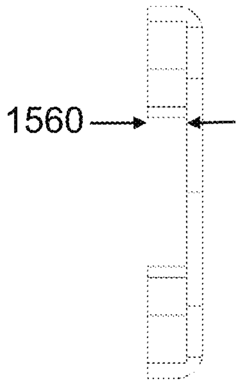
FIG. 19C
FIG. 19D

IMPLANT INSERTER ASSEMBLY

CROSS-REFERENCE TO RELATED APPLICATIONS

The present disclosure claims the benefit of U.S. Provisional Patent Application Ser. No. 63/544,538, filed on Oct. 17, 2023 and entitled IMPLANT INSERTER ASSEMBLY, which is incorporated by reference as though set forth herein in its entirety.

TECHNICAL FIELD

The present disclosure relates to systems and methods for use in orthopedic surgery. More specifically, the present disclosure relates to implant inserter assembly systems and surgical methods.

BACKGROUND

Spinal surgeries traditionally require sizable incisions to accommodate the instruments and implants necessary for precise placement and fixation. Despite advancements in minimally invasive techniques, current implant inserter assemblies still necessitate incisions of a significant size. This can prolong recovery times, increase the risk of complications such as infection, and cause discomfort for patients postoperatively. The size of the incision profoundly influences the invasiveness and outcomes of these surgeries. Minimally invasive surgical techniques have sought to reduce the impact of large incisions; however, existing implant inserter assemblies continue to require incisions of a certain size in order to effectively insert and position implants securely.

There is a need in the medical community for an implant inserter assembly capable of achieving precise implant placement without the requirement for a large incision. Such an innovation would not only enhance patient comfort and recovery but also mitigate surgical risks and complications associated with larger incisions. By enabling minimally invasive procedures that preserve tissue integrity and minimize trauma, this advancement could improve the outcomes of spinal surgery practices.

SUMMARY

The various systems and methods of the present disclosure have been developed in response to the present state of the art, and in particular, in response to the problems and needs in the art that have not yet been fully solved by currently available acetabular prosthetic systems and methods.

In some embodiments, a system for inserting an implant into an intervertebral space may include an implant inserter having a first arm, a second arm, and a first retention member. The first arm and the second arm may be moveable, relative to each other, between a locked configuration, in which the first arm and the second arm may be spaced apart such that the first arm and the second arm may be locked in place relative to the implant, and a compressed configuration, in which the first arm and the second arm may be less spaced apart such that the first arm and the second arm may be withdrawable from the implant. The first retention member may be moveable between a locked position, in which the first retention member may block relative motion of the first arm and the second arm from the locked configuration to the compressed configuration, and an unlocked position, in which the first retention member may not block relative motion of the first arm and the second arm from the locked configuration to the compressed configuration.

In the system of any preceding paragraph, the system may further include the implant. The implant may include a first recess configured to receive a first protruding feature on the first arm and a second recess configured to receive a second protruding feature on the second arm.

In the system of any preceding paragraph, the implant inserter may further include a third arm, a fourth arm, and a second retention member. The third arm and the fourth arm may be moveable, relative to each other, between a locked configuration, in which the third arm and the fourth arm may be spaced apart such that the third arm and the fourth arm may be locked in place relative to the implant, and a compressed configuration, in which the third arm and the fourth arm may be less spaced apart such that the third arm and the fourth arm may be withdrawable from the implant. The second retention member may be moveable between a locked position, in which the second retention member may block relative motion of the third arm and the fourth arm from the locked configuration to the compressed configuration, an unlocked position in which the second retention member may not block relative motion of the third arm and the fourth arm from the locked configuration to the compressed configuration.

In the system of any preceding paragraph, the implant may further include a third recess configured to receive a third protruding feature on the third arm and a fourth recess configured to receive a fourth protruding feature on the fourth arm.

In the system of any preceding paragraph, the implant may further include an implant width measured at a widest portion of the implant. The implant inserter may further include a first distance between the first arm and the third arm in the locked configuration, and a second distance between the first arm and the third arm in the compressed configuration. The first distance and the second distance may be less than or equal to the implant width.

In the system of any preceding paragraph, a first distance between the first arm and the third arm and a second distance between the second arm and the fourth arm may be generally equal in the locked configuration as in the compressed configuration.

In the system of any preceding paragraph, the first arm and the second arm may be further moveable, relative to each other, along a first direction between the locked configuration and the compressed configuration and the first direction may be transverse to a second direction along which the first arm and the second arm may be withdrawable from the implant in the compressed configuration.

In the system of any preceding paragraph, the system may further include the implant. The implant may include a first recess extending parallel to the first direction to receive a first protruding feature on the first arm and a second recess extending parallel to the first direction to receive a second protruding feature on the second arm.

In some embodiments, a system for inserting an implant into an intervertebral space may include an implant inserter. The implant inserter may include a first arm, a second arm, a third arm, a fourth arm, a first retention member, and a second retention member. The first arm and the second arm may be moveable, relative to each other, and the third arm and the fourth arm may be moveable, relative to each other, between a locked configuration, in which the first arm may be spaced apart from the second arm and the third arm may be spaced apart from the fourth arm, such that the first arm, the second arm, the third arm, and the fourth arm may be locked in place relative to the implant, and a compressed configuration, in which the first arm may be less spaced apart from the second arm and the third arm may be less spaced apart from the fourth arm, such that the first arm, the second arm, the third arm, and the fourth arm may be withdrawable from the implant. A first distance between the first arm and the third arm and a second distance between the second arm and the fourth arm may be generally equal in the locked configuration as in the compressed configuration.

In the system of any preceding paragraph, the system further including the implant. The implant may include a first recess configured to receive a first protruding feature on the first arm, a second recess configured to receive a second protruding feature on the second arm, a third recess configured to receive a third protruding feature on the third arm, and a fourth recess configured to receive a fourth protruding feature on the fourth arm.

In the system of any preceding paragraph, the first arm and the second arm may be further moveable, relative to each other, along a first direction between the locked configuration and the compressed configuration. The third arm and the fourth arm may be further moveable, relative to each other, along the first direction between the locked configuration and the compressed configuration. The first direction may be transverse to a second direction along which the first arm, the second arm, the third arm, and the fourth arm are withdrawable from the implant in the compressed configuration.

A first distance between the first arm and the third arm and a second distance between the second arm and the fourth arm may be generally the same in the locked configuration as in the compressed configuration.

In the system of any preceding paragraph, the system may further include the implant. The implant may include a first recess extending parallel to the first direction to receive a first protruding feature on the first arm, a second recess extending parallel to the first direction to receive a second protruding feature on the second arm, a third recess extending parallel to the first direction to receive a third protruding feature on the third arm, and a fourth recess extending parallel to the first direction to receive a fourth protruding feature on the second arm.

In the system of any preceding paragraph, the implant inserter may further include a first retention member and a second retention member. The first retention member and the second retention member may be moveable between a locked position, in which the first retention member may block relative motion of the first arm and the second arm from the locked configuration to the compressed configuration, and an unlocked position, in which the first retention member may not block relative motion of the first arm and the second arm from the locked configuration to the compressed configuration.

In the system of any preceding paragraph, the system further including the implant. The implant may include an implant width measured at a widest portion of the implant. The implant inserter may further include a first distance between the first arm and the third arm in the locked configuration and a second distance between the first arm and the third arm in the compressed configuration. The first distance and the second distance may be less than or equal to the implant width.

In some embodiments, a system for inserting an implant into an intervertebral space may include the implant having an implant width measured at a widest portion of the implant and an implant inserter. The implant inserter may include a first arm, a second arm, a third arm, and a fourth arm. The first arm and the second arm may be moveable, relative to each other, and the third arm and the fourth arm may be moveable, relative to each other, between a locked configuration, in which the first arm may be spaced apart from the second arm and the third arm may be spaced apart from the fourth arm, such that the first arm, the second arm, the third arm, and the fourth arm may be locked in place relative to the implant, and a compressed configuration, in which the first arm may be less spaced apart from the second arm and the third arm may be less spaced apart from the fourth arm, such that the first arm, the second arm, the third arm, and the fourth arm may be withdrawable from the implant. The implant inserter may further include a first distance between the first arm and the third arm in the locked configuration and a second distance between the first arm and the third arm in the compressed configuration. The first distance and the second distance may be less than or equal to the implant width.

In the system of any preceding paragraph, the implant may further include a first recess configured to receive a first protruding feature on the first arm, a second recess configured to receive a second protruding feature on the second arm, a third recess configured to receive a third protruding feature on the third arm, and a fourth recess configured to receive a fourth protruding feature on the fourth arm.

In the system of any preceding paragraph, the first arm and the second arm may be further moveable, relative to each other, along a first direction between the locked configuration and the compressed configuration. The third arm and the fourth arm may be further moveable, relative to each other, along the first direction between the locked configuration and the compressed configuration. The first direction may be transverse to a second direction along which the first arm, the second arm, the third arm, and the fourth arm may be withdrawable from the implant in the compressed configuration.

In the system of any preceding paragraph, the implant may further include a first recess extending parallel to the first direction to receive a first protruding feature on the first arm, a second recess extending parallel to the first direction to receive a second protruding feature on the second arm, a third recess extending parallel to the first direction to receive a third protruding feature on the third arm, and a fourth recess extending parallel to the first direction to receive a fourth protruding feature on the second arm.

In the system of any preceding paragraph, the implant inserter may further include a first retention member and a second retention member. The first retention member and the second retention member may be moveable between a locked position, in which the first retention member may block relative motion of the first arm and the second arm from the locked configuration to the compressed configuration, and an unlocked position, in which the first retention member may not block relative motion of the first arm and the second arm from the locked configuration to the compressed configuration.

In the system of any preceding paragraph, a first distance between the first arm and the third arm and a second distance between the second arm and the fourth arm may be generally equal in the locked configuration as in the compressed configuration.

These and other features and advantages of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through the use of accompanying drawings.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the disclosure will be described with additional specificity and detail through use of the accompanying drawings in which:

FIG. 19A is a top view of a carriage sideplate of the spike carriage assembly of FIG. 1 according to an embodiment;

FIG. 19B is a perspective view of the carriage sideplate of FIG. 19A;

FIG. 19C is a front view of the carriage sideplate of FIG. 19A;

FIG. 19D is a right-side view of the carriage sideplate of FIG. 19A;

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, system, and method, as represented in FIGS. 1 through 22D, is not intended to limit the scope of the claims, but is merely representative of exemplary embodiments of the present disclosure.

The phrases “connected to,” “coupled to” and “in communication with” refer to any form of interaction between two or more entities, including mechanical, electrical, magnetic, electromagnetic, fluid, and thermal interaction. Two components may be functionally coupled to each other even though they are not in direct contact with each other. The term “abutting” refers to items that are in direct physical contact with each other, although the items may not necessarily be attached together.

The word “exemplary” is used herein to mean “serving as an example, instance, or illustration.” Any embodiment described herein as “exemplary” is not necessarily to be construed as preferred or advantageous over other embodiments. While the various aspects of the embodiments are presented in drawings, the drawings are not necessarily drawn to scale unless specifically indicated.

Not every feature of each embodiment is labeled in every figure in which that embodiment appears, in order to keep the figures clear. Similar reference numbers (for example, those that are identical except for the first numeral) may be used to indicate similar features in different embodiments.

Any of the devices described herein may be fabricated from metals, alloys, polymers, plastics, ceramics, glasses, composite materials, or combinations thereof, including but not limited to stainless steel, aluminum, titanium, titanium alloy, PEEK (polyether ether ketone), polycarbonate, ABS (acrylonitrile butadiene styrene), polyamide, acetal, acetal copolymer, among others. Different materials may be used within a single part.

Figure 1:
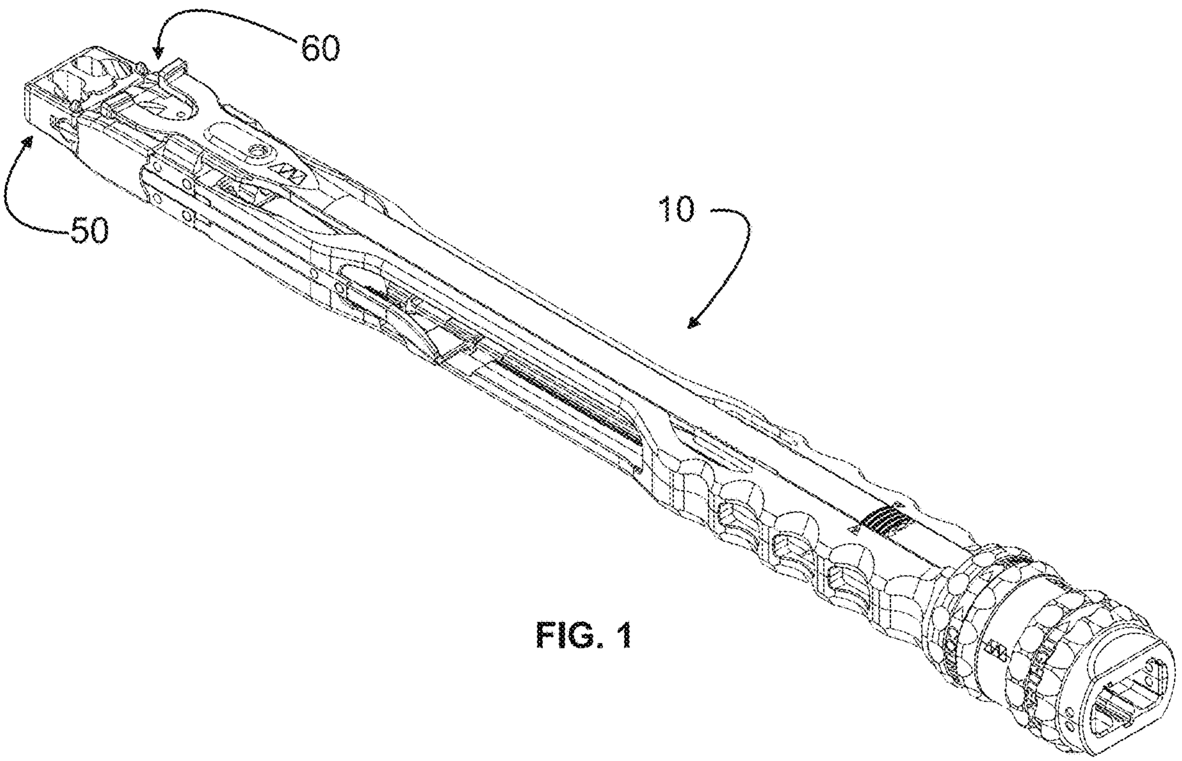
FIG. 1 is a perspective view of an implant inserter assembly connected to a spike carriage assembly and an implant assembly according to an embodiment.

FIG. 1 is a perspective view of an implant inserter assembly 10 connected to a spike carriage assembly 60 and an implant assembly 50 according to an embodiment. The implant inserter assembly 10 may be configured to facilitate insertion and positioning of an intervertebral spacer. Additionally, or alternatively, the intervertebral spacer may be configured to stabilize a joint between a superior vertebra and an inferior vertebra. Additionally, or alternatively, the implant inserter assembly 10 may be configured to facilitate insertion and positioning of an implant assembly 50 configured for implantation in a cervical spine of a patient.

The implant inserter assembly 10 may further be configured to functionally engage a spike carriage assembly 60 which may be configured to facilitate deployment of superior fasteners (not shown) and/or inferior fasteners (not shown) through the spike carriage assembly 60, through an implant assembly 50, and into a vertebra to secure the implant assembly 50 to the vertebra and prevent expulsion and/or subsidence of the implant assembly 50. The implant inserter assembly 10 may be configured to facilitate deployment of one or more superior fasteners (not shown) and/or one or more inferior fasteners (not shown).

The implant inserter assembly may include a first arm, a second arm, and a first retention member. The implant inserter assembly 10 may have a locked configuration, in which the first arm and the second arm are spaced apart such that the first arm and the second arm are locked in place relative to the implant. Additionally, the implant inserter assembly may have an unlocked configuration, in which the first arm and the second arm are less spaced apart such that the first arm and the second arm are withdrawable from the implant.

Figure 2:
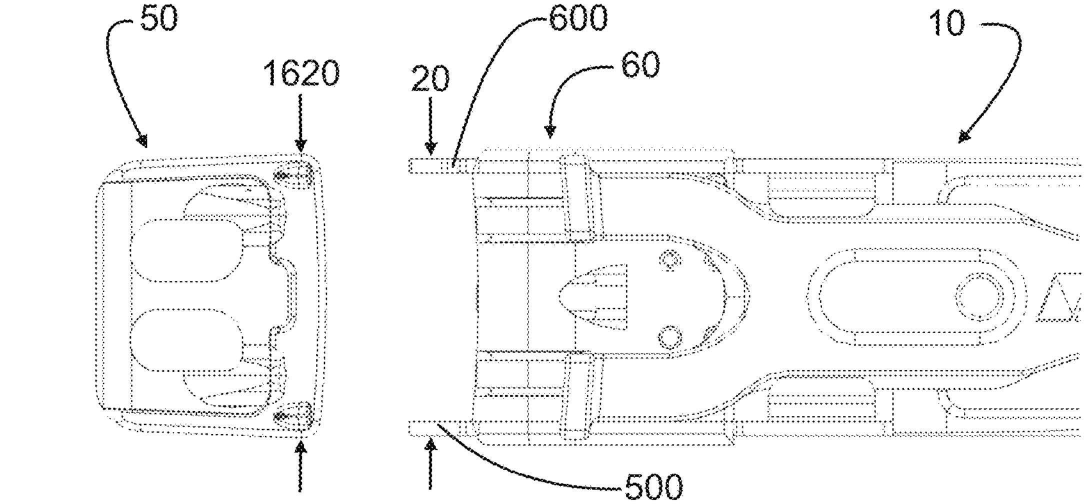
FIG. 2 is a partial top view of the implant inserter assembly connected to the spike carriage assembly of FIG. 1 and not connected to the implant assembly of FIG. 1.

FIG. 2 is a partial top view of the implant inserter assembly 10 connected to the spike carriage assembly 60 and not connected to the implant assembly 50. The implant inserter assembly 10 may include one or more round retention arms 500 and one or more sharp retention arms 600. In an assembled state, the one or more round retention arms 500 may be mounted to a first side of a distal end of the implant inserter assembly 10. The one or more sharp retention arms 600 may be mounted to a second side of a distal end of the implant inserter assembly 10 that is opposite the first side. The one or more round retention arms 500 and the one or more sharp retention arms 600 may be separated by a retention arm width 20.

The implant assembly 50 may include a plate 1600 and a body 1700. The implant assembly 50 may include a plate width 1620 (or implant width) that may equal the widest portion of the implant assembly 50. The retention arm width 20 may be less than or equal to the plate width 1620 of the implant assembly 50. Alternatively, the retention arm width 20 may be less than 120% of the plate width 1620 of the implant assembly 50. Alternatively, the retention arm width 20 may be less than 150% of the plate width 1620 of the implant assembly 50.

An implant inserter assembly 10 may be configured to engage an implant assembly 50 wherein the retention arm width 20 remains generally unchanged before, during and after engagement of the implant inserter assembly 10 with the implant assembly 50. The implant inserter assembly 10 may be configured to engage the implant assembly 50 with no increase in the retention arm width 20. The implant inserter assembly 10 may be configured to disengage the implant assembly 50 with no increase in the retention arm width 20. The implant inserter assembly 10 may be configured to engage the implant assembly 50 with no decrease in the retention arm width 20. The implant inserter assembly 10 may be configured to disengage the implant assembly 50 with no decrease in the retention arm width 20.

The implant inserter assembly 10 may include a retention arm width 20. The retention arm width 20 may be defined as a distance between a round retention arm 500 and a sharp retention arm 600 in the locked configuration. The retention arm width 20 may be less than or equal to the plate width 1620. Additionally, or alternatively, the retention arm width 20 may be defined as a distance between a round retention arm 500 and a sharp retention arm 600 in the compressed configuration. The retention arm width 20 may be less than or equal to the plate width 1620.

Figure 3:
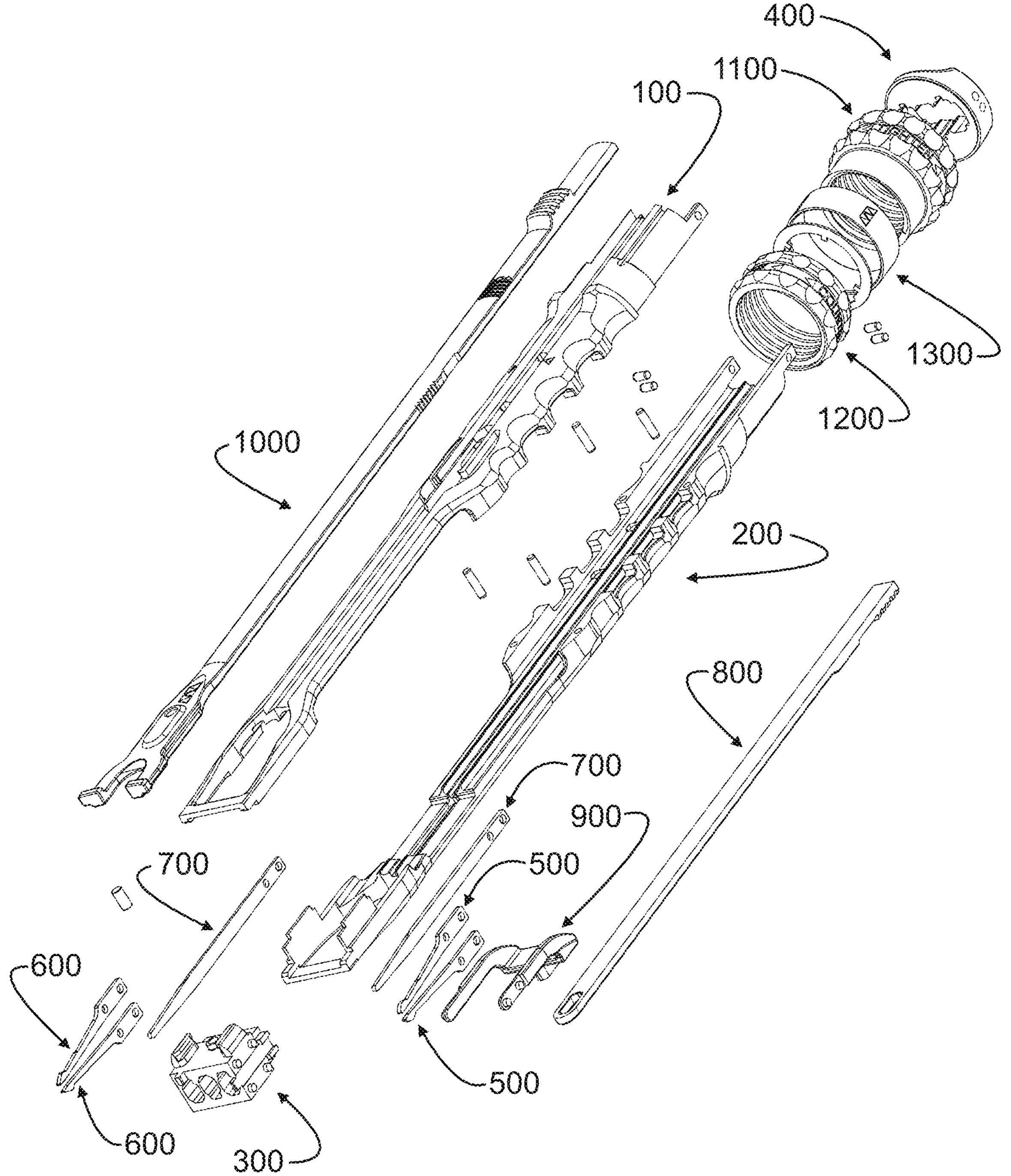
FIG. 3 is a perspective exploded view of the implant inserter assembly of FIG. 1.

FIG. 3 is a perspective exploded view of the implant inserter assembly 10 according to an embodiment. The implant inserter assembly 10 may include an inserter body top 100, an inserter body bottom 200, an inserter body head 300, an inserter body cap 400, one or more round retention arms 500, one or more sharp retention arms 600, one or more retention wedges 700, a wedge actuator 800, an actuator yoke 900, a depth-stop 1000, a lock ring 1100, a depth ring 1200, and a slip ring 1300. The implant inserter assembly 10 may include additional components (such as dowel pins and/or step pins) to facilitate assembly of the components.

Figure 4A:
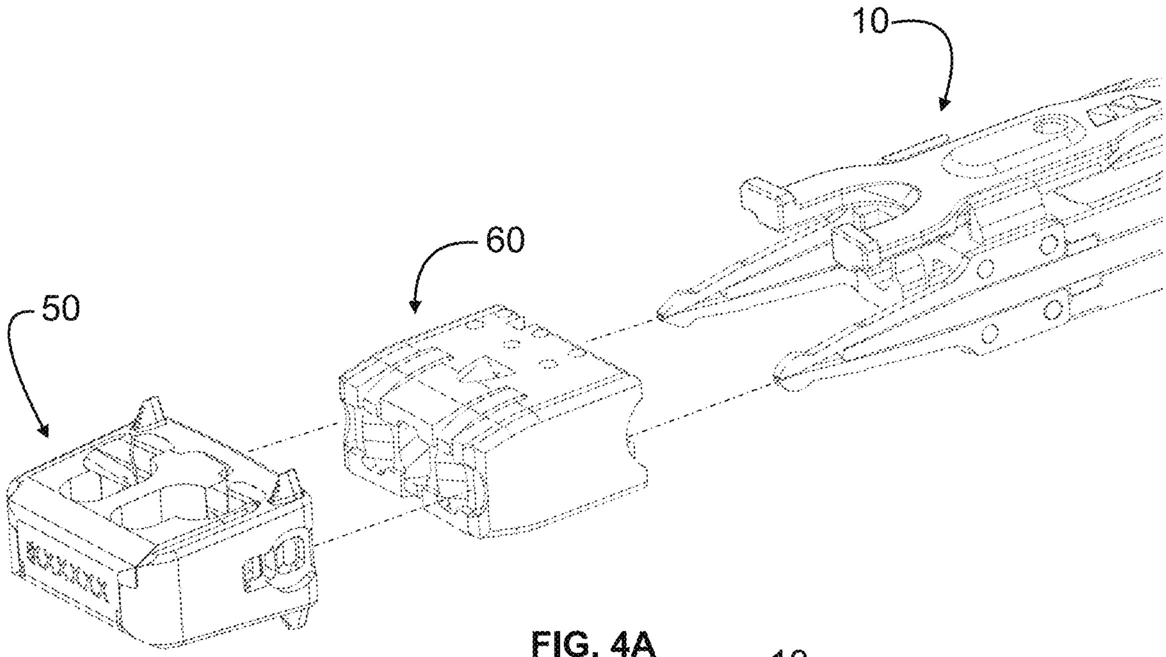
FIG. 4A is a perspective view of the implant inserter assembly, the spike carriage assembly and the implant assembly of FIG. 1 in a disconnected state.

FIG. 4A is a perspective view of an implant inserter assembly 10, a spike carriage assembly 60 and an implant assembly 50, according to an embodiment, in a disconnected state. The spike carriage assembly 60 may include a spike carriage 1400 and one or more carriage sideplates 1500. The spike carriage assembly 60 may be configured to retain one or more superior fasteners (not shown) and/or one or more inferior fasteners (not shown) prior to deployment of the one or more superior fasteners (not shown) and/or one or more inferior fasteners (not shown) through an implant assembly 50, and into a vertebra. The spike carriage assembly 60 may be configured with a first arm channel 1550 on a first side and a second arm channel 1550' on a second side. The first arm channel 1550 on the first side may be configured to slidably receive one or more round retention arms 500. The second arm channel 1550' on the second side may be configured to slidably receive one or more sharp retention arms 600. The spike carriage assembly 60 may be further configured such that, when the spike carriage assembly 60 is fully engaged with the implant inserter assembly 10, the retention profiles 520 of the one or more round retention arms 500 and the retention profiles 620 of the one or more sharp retention arms 600 extend beyond a distal end of the spike carriage assembly 60 and may engage the implant assembly 50.

Figure 4B:
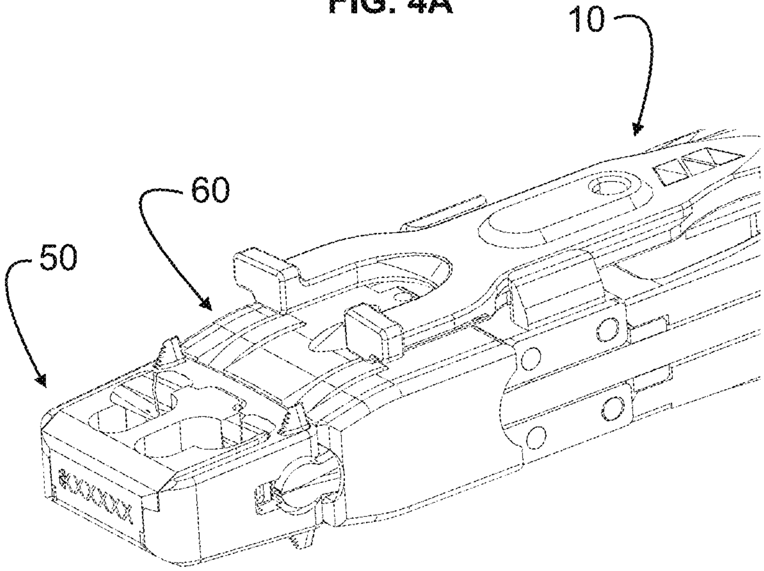
FIG. 4B is a perspective view of the implant inserter assembly, the spike carriage assembly and the implant assembly of FIG. 1 in a connected state.
Figure 4C:
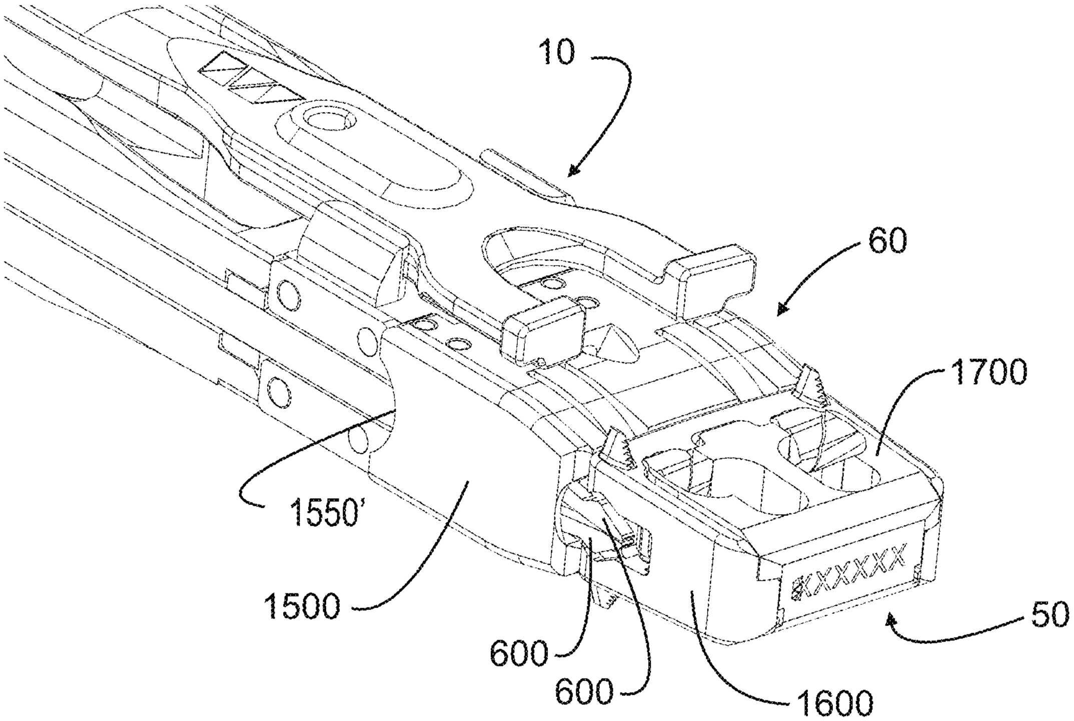
FIG. 4C is a perspective view of the implant inserter assembly, the spike carriage assembly and the implant assembly of FIG. 1 in a connected state.
Figure 4D:
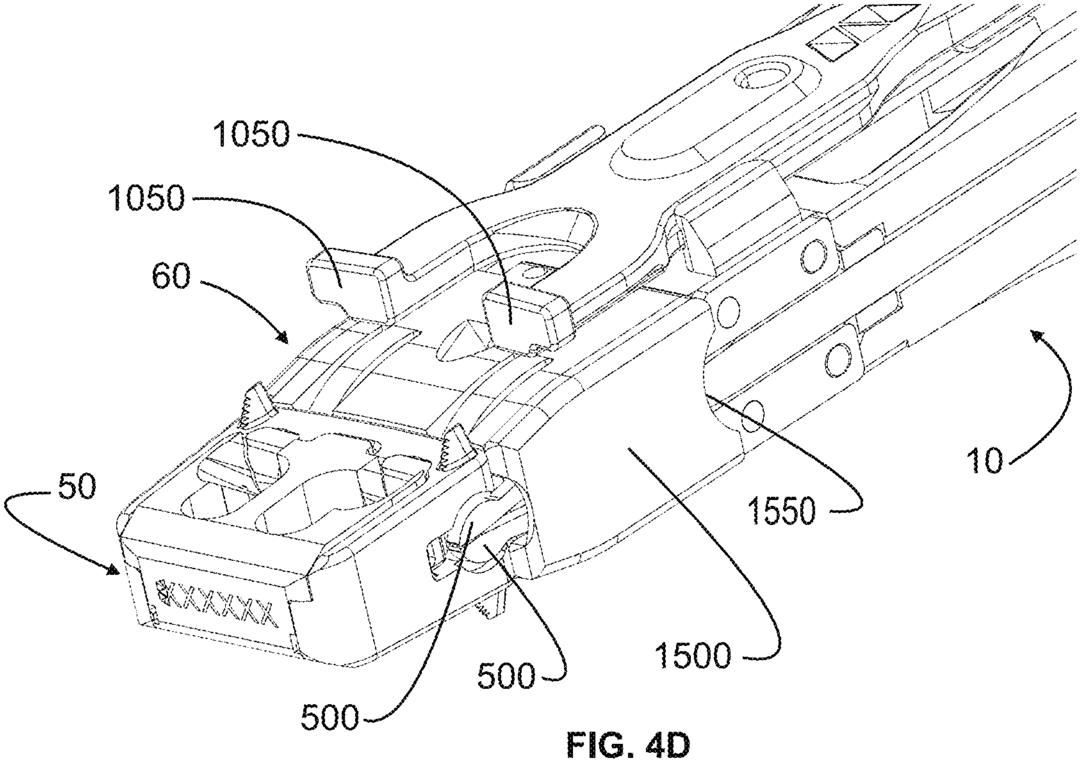
FIG. 4D is a perspective view of the implant inserter assembly, the spike carriage assembly and the implant assembly of FIG. 1 in a connected state.

FIG. 4B, FIG. 4C, and FIG. 4D are each a perspective view of an implant inserter assembly 10, a spike carriage assembly 60 and an implant assembly 50, according to an embodiment, in a connected state. The implant inserter assembly 10 may include a connected state wherein the implant inserter assembly 10 is securely connected to an implant assembly 50. The implant inserter assembly 10 may include a connected state wherein the implant inserter assembly 10 is securely connected to an implant assembly 50 and a spike carriage assembly 60. The implant inserter assembly 10 may include a disconnected state wherein the implant inserter assembly 10 is not connected to an implant assembly 50. The implant inserter assembly 10 may include a disconnected state wherein the implant inserter assembly 10 is not connected to an implant assembly 50 nor a spike carriage assembly 60.

The implant inserter assembly 10 may include a depth-stop 1000. The depth-stop 1000 may be configured to limit the depth an implant assembly 50 may be deployed within an intervertebral space. The depth-stop 1000 may be configured to translate linearly in a direction generally parallel to a longitudinal axis of the implant inserter assembly 10. The implant inserter assembly 10 may include a wedge actuator 800 configured to translate linearly in a direction generally parallel to the longitudinal axis of the implant inserter assembly 10. The implant inserter assembly 10 may be configured so that the position of the depth-stop 1000 may be adjusted at a proximal end of the implant inserter assembly 10. The implant inserter assembly 10 may be configured so that the position of the wedge actuator 800 may be adjusted at the proximal end of the implant inserter assembly 10.

A depth-stop 1000 may include one or more stop faces 1050. The implant inserter assembly 10 may be configured so that the one or more stop faces 1050 may contact a superior vertebra or an inferior vertebra to limit the deployment depth of the implant assembly 50 during deployment of an implant assembly 50 into the intervertebral space. The depth-stop 1000 and the implant inserter assembly 10 may be configured so that the position of the depth-stop 1000 may be adjustable from a first position to a second position defining a first distance and a second distance, wherein the first distance may be the distance from the one or more stop faces 1050 with the depth-stop 1000 in the first position to the distal end of the implant assembly 50 and the second distance may be the distance from the one or more stop faces 1050 with the depth-stop 1000 in the second position to the distal end of the implant assembly 50. The depth-stop 1000 and the implant inserter assembly 10 may be configured so that the first distance is less than the second distance. The depth-stop 1000 and the implant inserter assembly 10 may be further configured so that the first distance is greater than the distance from a proximal end of the implant assembly 50 to a distal end of the implant assembly 50.

Figure 5A:
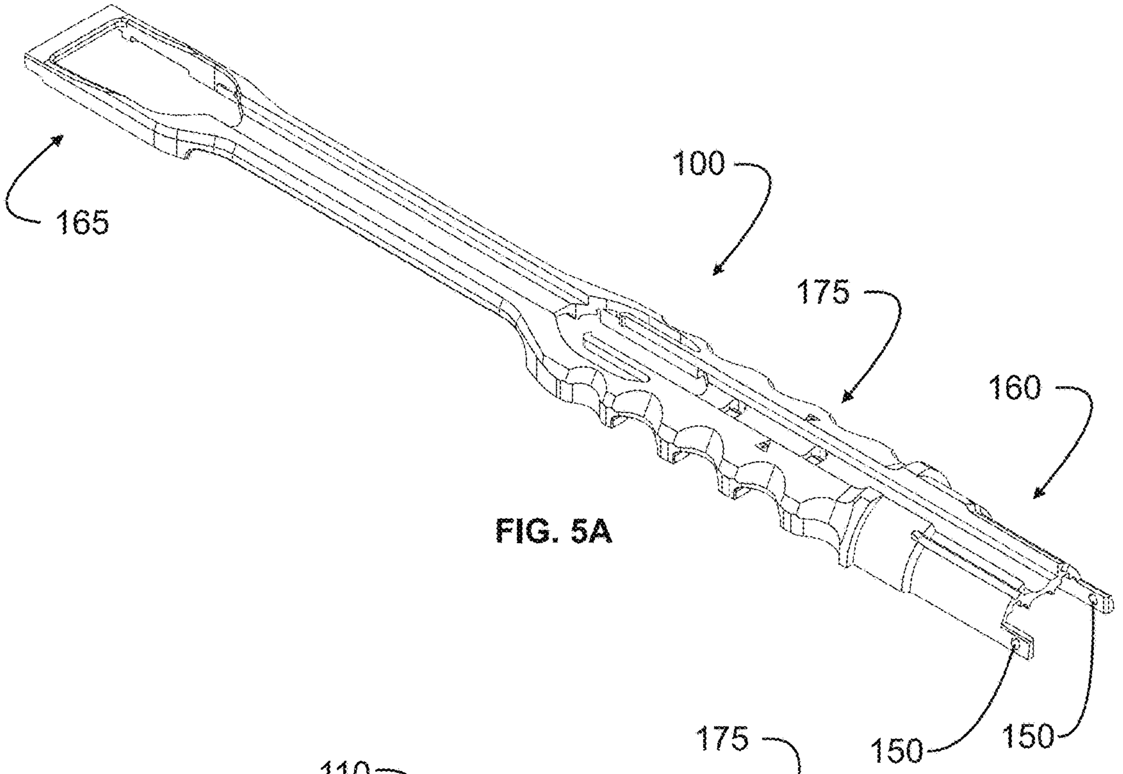
FIG. 5A is a perspective view of an inserter body top of the implant inserter assembly of FIG. 1 according to an embodiment.
Figure 5B:
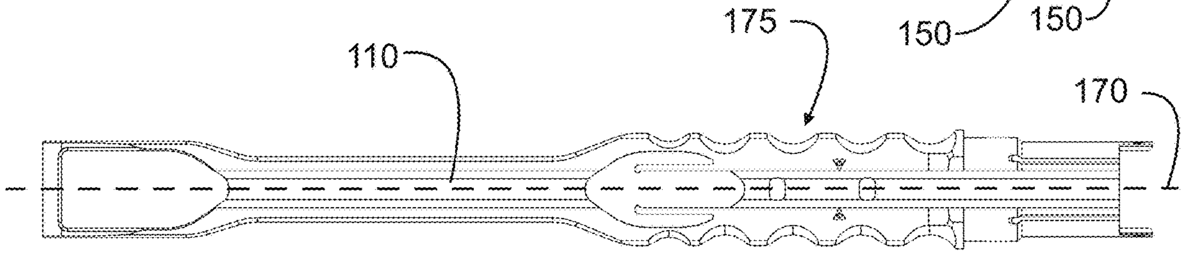
FIG. 5B is a top view of the inserter body top of FIG. 5A.
Figure 5C:
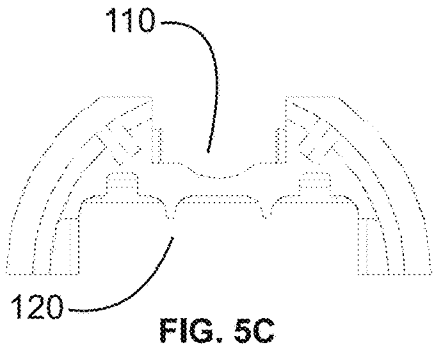
FIG. 5C is a right-side view of the inserter body top of FIG. 5A.

FIG. 5A is a perspective view of an inserter body top 100 of an implant inserter assembly 10 according to an embodiment. FIG. 5B is a top view of the inserter body top 100 and FIG. 5C is a right-side view of the inserter body top 100. The inserter body top 100 may include a proximal portion 160, a distal portion 165, and an axis 170 along the length of the inserter body top 100. Additionally, the axis 170 may be parallel to a longitudinal axis of the implant inserter assembly 10. The inserter body top 100 may include a grip portion 175 in the proximal portion 160.

The inserter body top 100 may further include a top channel 110; a central channel 120 and one or more pin holes 150. The top channel 110 may be configured to be generally parallel to the axis 170 along the length of the inserter body top 100. The top channel 110 may be configured to slidably receive a depth-stop 1000. The central channel 120 may be generally parallel to the axis 170 along the length of the inserter body top 100. The central channel 120 may further be configured to slidably receive one or more drivers (not shown) configured to engage one or more superior fasteners (not shown) and/or inferior fasteners (not shown) to facilitate deployment of the one or more superior fasteners (not shown) and/or one or more inferior fasteners (not shown) through a spike carriage assembly 60, through an implant assembly 50, and into a vertebra to secure an implant assembly 50 to the vertebra and prevent expulsion and/or subsidence of the implant assembly 50. The one or more pin holes 150 may be configured to receive one or more fasteners to secure the inserter body top 100 to an inserter body cap 400.

Figure 6A:
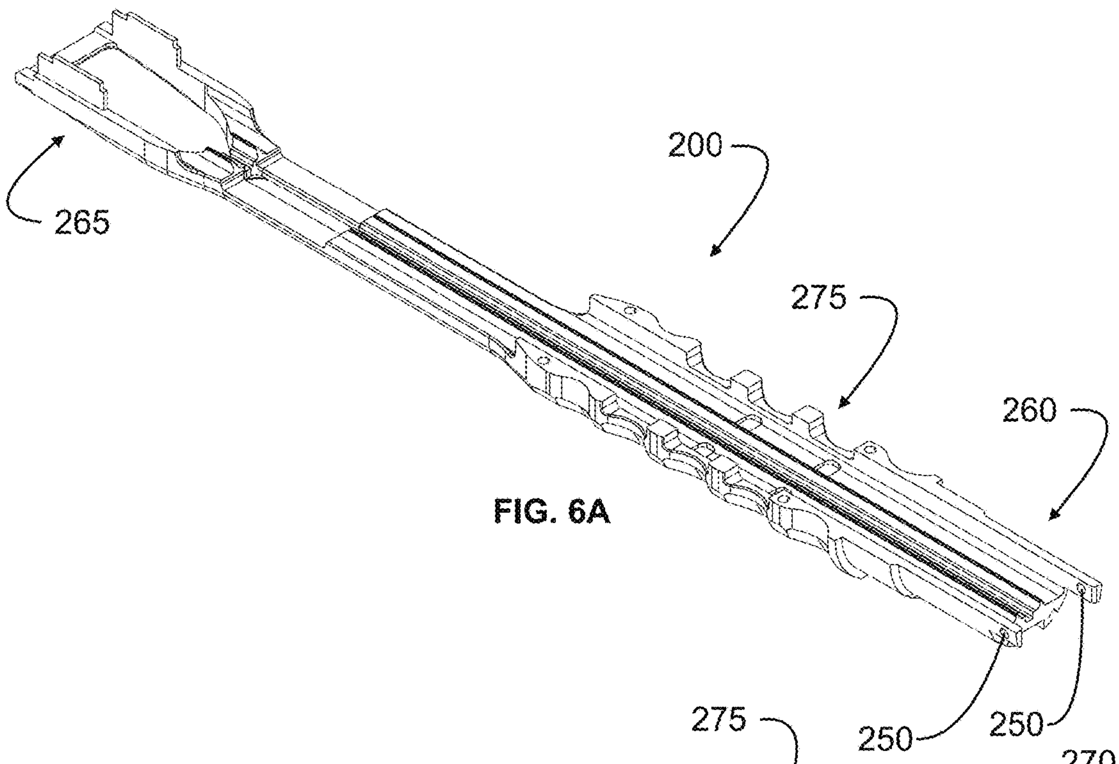
FIG. 6A is a perspective view of an inserter body bottom of the implant inserter assembly of FIG. 1 according to an embodiment.
Figure 6B:
FIG. 6B is a top view of the inserter body bottom of FIG. 6A.
Figure 6C:
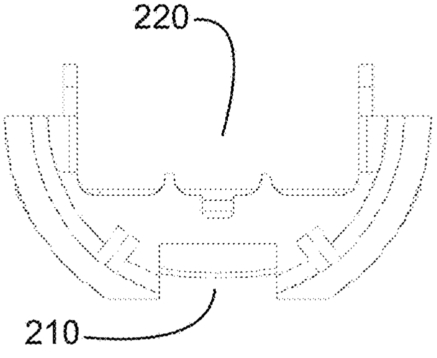
FIG. 6C is a right-side view of the inserter body bottom of FIG. 6A.

FIG. 6A is a perspective view of an inserter body bottom 200 of an implant inserter assembly 10 according to an embodiment. FIG. 6B is a top view of the inserter body bottom 200 and FIG. 6C is a right-side view of the inserter body bottom 200. The inserter body bottom 200 may include a proximal portion 260; a distal portion 265; and an axis 270 along the length of the inserter body bottom 200. The inserter body bottom 200 may include a grip portion 275 in the proximal portion 260. The inserter body bottom 200 may further include a bottom channel 210; a central channel 220 and one or more pin holes 250. The bottom channel 210 may be configured to be generally parallel to the axis 270 along the length of the inserter body bottom 200. The bottom channel 210 may be configured to slidably receive a wedge actuator 800. The central channel 220 may be generally parallel to the axis 270 along the length of the inserter body bottom 200. The central channel 220 may further be configured to slidably receive one or more drivers (not shown) configured to engage one or more superior fasteners (not shown) and/or inferior fasteners (not shown) to facilitate deployment of the one or more superior fasteners (not shown) and/or one or more inferior fasteners (not shown) through a spike carriage assembly 60, through an implant assembly 50, and into a vertebra to secure an implant assembly 50 to the vertebra and prevent expulsion and/or subsidence of the implant assembly 50. The one or more pin holes 250 may be configured to receive one or more fasteners to secure the inserter body bottom 200 to an inserter body cap 400.

Figure 7A:
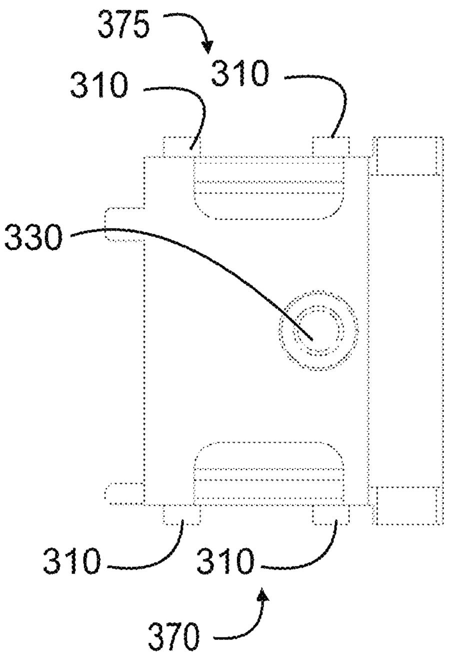
FIG. 7A is a top view of an inserter body head of the implant inserter assembly of FIG. 1 according to an embodiment.
Figure 7B:
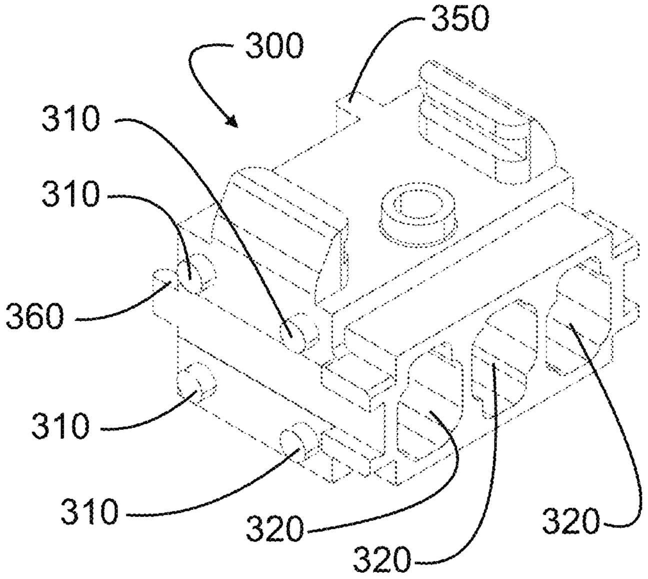
FIG. 7B is a perspective view of the inserter body head of FIG. 7A.
Figure 7C:
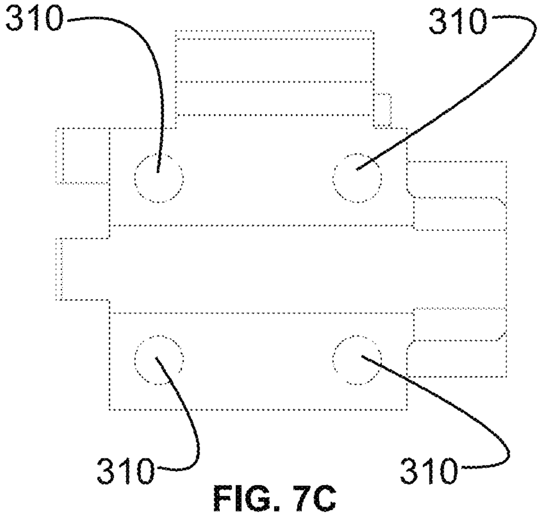
FIG. 7C is a front view of the inserter body head of FIG. 7A.
Figure 7D:
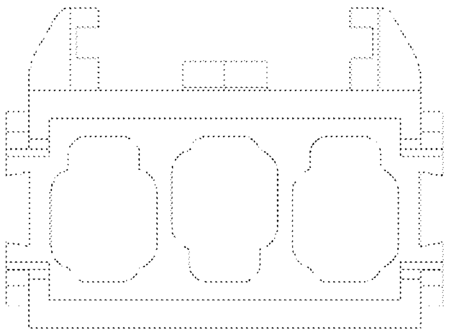
FIG. 7D is a right-side view of the inserter body head of FIG. 7A.

FIG. 7A is a top view of an inserter body head 300 of an implant inserter assembly 10 according to an embodiment. FIG. 7B is a perspective view of the inserter body head 300, FIG. 7C is a front view of the inserter body head 300, and FIG. 7D is a right-side view of the inserter body head 300. The inserter body head 300 may be configured to securably connect to the distal portion 165 of the inserter body top 100 and the distal portion 265 of the inserter body bottom 200. The inserter body head 300 may include a first locating feature 350 and a second locating feature 360. The first locating features 350 may be configured to engage a first locating notch 1450 and the second locating feature 360 may be configured to engage a second locating notch 1460. Additionally, the first locating feature 350; the second locating feature 360; the first locating notch 1450; and the second locating notch 1460 may be configured so that a spike carriage assembly 60 may engage the inserter body head 300 in a single orientation. Alternately, the first locating feature 350; the second locating feature 360; the first locating notch 1450; and the second locating notch 1460 may be configured so that a spike carriage assembly 60 may engage the inserter body head 300 in a plurality of orientations.

The inserter body head 300 may include one or more guide channels 320 configured to align with the central channel 120 and the central channel 220. The one or more guide channels 320 may further be configured to slidably receive one or more drivers (not shown) configured to engage one or more superior fasteners (not shown) or inferior fasteners (not shown) to facilitate deployment of the one or more superior fasteners (not shown) and/or one or more inferior fasteners (not shown) through a spike carriage assembly 60, through an implant assembly 50, and into a vertebra to secure an implant assembly 50 to the vertebra and prevent expulsion and/or subsidence of the implant assembly 50.

The inserter body head 300 may include one or more mounting pins 310. The one or more mounting pins 310 may be configured to securely engage one or more mounting holes 550 of one or more round retention arms 500 and one or more mounting holes 650 of one or more sharp retention arms 600. The inserter body head 300 may include one or more mounting pins 310 located on opposing sides of the inserter body head 300. The inserter body head 300 and the one or more mounting pins 310 may be configured so that one or more round retention arms 500 may be securely engaged to a first side 370 of the inserter body head 300 and one or more sharp retention arms 600 may be securely engaged to a second side 375 of the inserter body head 300 opposite the first side 370, wherein the distance between the one or more round retention arms 500 and the one or more sharp retention arms 600 is a retention arm width 20. In an embodiment, an inserter body head 300 may include a boss 330 configured to slidably engage a locating slot 1040 of a depth-stop 1000. The boss 330 may be configured to limit the position of a depth-stop 1000 between a first position and a second position.

Figure 8A:
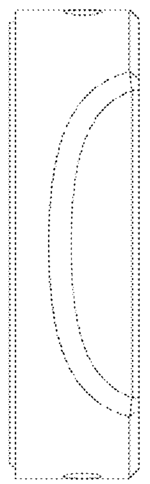
FIG. 8A is a top view of an inserter body cap of the implant inserter assembly of FIG. 1 according to an embodiment.
Figure 8B:
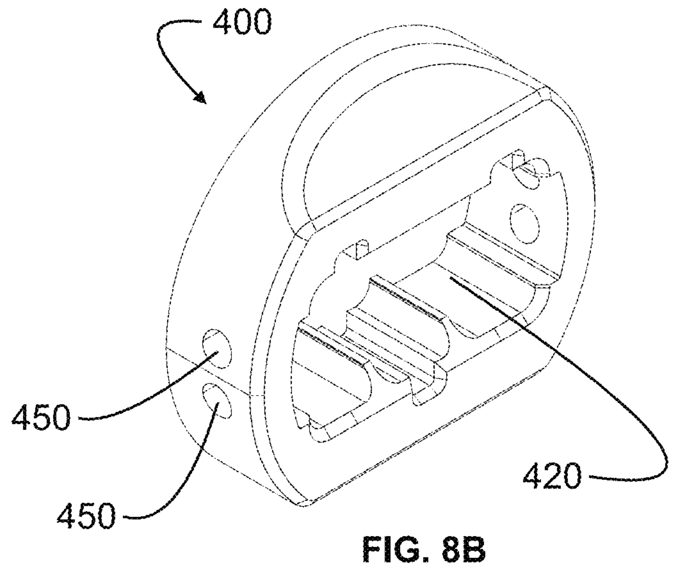
FIG. 8B is a perspective view of the inserter body cap of FIG. 8A.
Figure 8C:
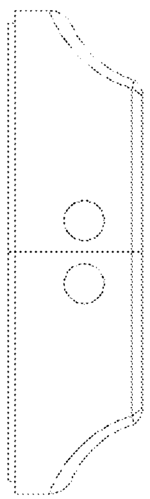
FIG. 8C is a front view of the inserter body cap of FIG. 8A.
Figure 8D:
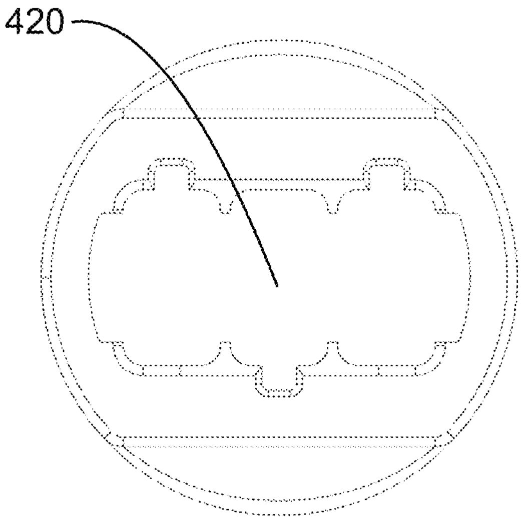
FIG. 8D is a right-side view of the inserter body cap of FIG. 8A.

FIG. 8A is a top view of an inserter body cap 400 of an implant inserter assembly 10 according to an embodiment. FIG. 8B is a perspective view of the inserter body cap 400, FIG. 8C is a front view of the inserter body cap 400, and FIG. 8D is a right-side view of the inserter body cap 400. The inserter body cap 400 may include a central channel 420. The central channel 420 may be configured to slidably receive one or more drivers (not shown) configured to engage one or more superior fasteners (not shown) or inferior fasteners (not shown) to facilitate deployment of the one or more superior fasteners (not shown) and/or one or more inferior fasteners (not shown) through a spike carriage assembly 60, through an implant assembly 50, and into a vertebra to secure an implant assembly 50 to the vertebra and prevent expulsion and/or subsidence of the implant assembly 50. The inserter body cap 400 may include one or more pin holes 450. The one or more pin holes 450 may be configured to receive one or more fasteners to secure the inserter body top 100 and the inserter body bottom 200 to the inserter body cap 400.

Figure 9A:
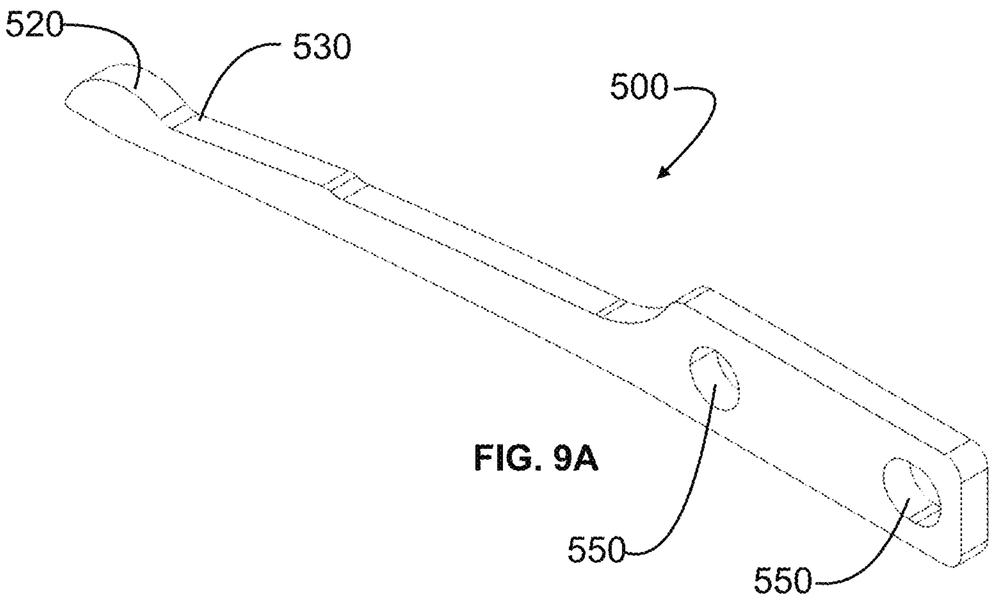
FIG. 9A is a perspective view of a round retention arm of the implant inserter assembly of FIG. 1 according to an embodiment.
Figure 9B:
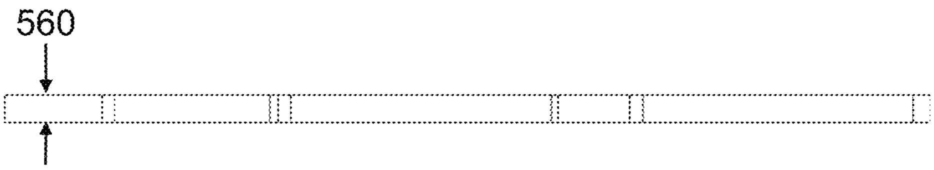
FIG. 9B is a top view of the round retention arm of FIG. 9A.
Figure 9C:
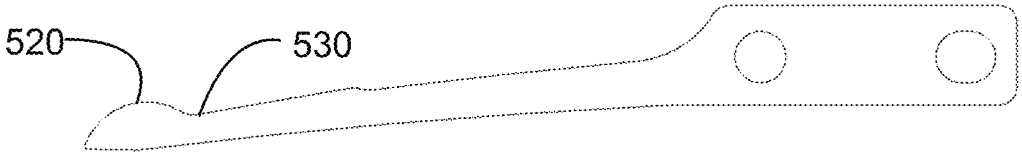
FIG. 9C is a front view of the round retention arm of FIG. 9A.

FIG. 9A is a perspective view of a round retention arm 500 of an implant inserter assembly 10 according to an embodiment. FIG. 9B is a top view of the round retention arm 500 and FIG. 9C is a front view of the round retention arm 500. The round retention arm 500 may include a retention profile 520, a recessed portion 530, and mounting holes 550.

One or more round retention arms 500 may be coupled to the inserter body head 300 so that the one or more round retention arms 500 may be moveable relative to each other. The one or more round retention arms 500 may be moveable, relative to each other, along a first direction between the locked configuration and the unlocked configuration. Additionally, the first direction may be transverse to a second direction along which the one or more round retention arms 500, in the unlocked configuration, may be withdrawable from the implant assembly 50. The retention profile 520 may be configured as a protruding feature on the round retention arm 500.

The retention profile 520 of the round retention arm 500 may be different than the retention profile 620 of the sharp retention arm 600. The retention profile 520 and the retention profile 620 may be configured so that one or more round retention arms 500 and one or more sharp retention arms 600 engage an implant assembly 50 when the implant assembly 50 is in a single orientation, i.e.: the implant assembly 50 may be load onto the implant inserter assembly 10 in a single orientation. Alternatively, the retention profile 520 and the retention profile 620 may each be configured so that one or more round retention arms 500 and one or more sharp retention arms 600 engage an implant assembly 50 when the implant assembly 50 is in a plurality of orientations. The round retention arm 500 may include an arm thickness 560 configured to be slidably received in a first arm channel 1550 of a first carriage sideplate 1500.

Figure 10A:
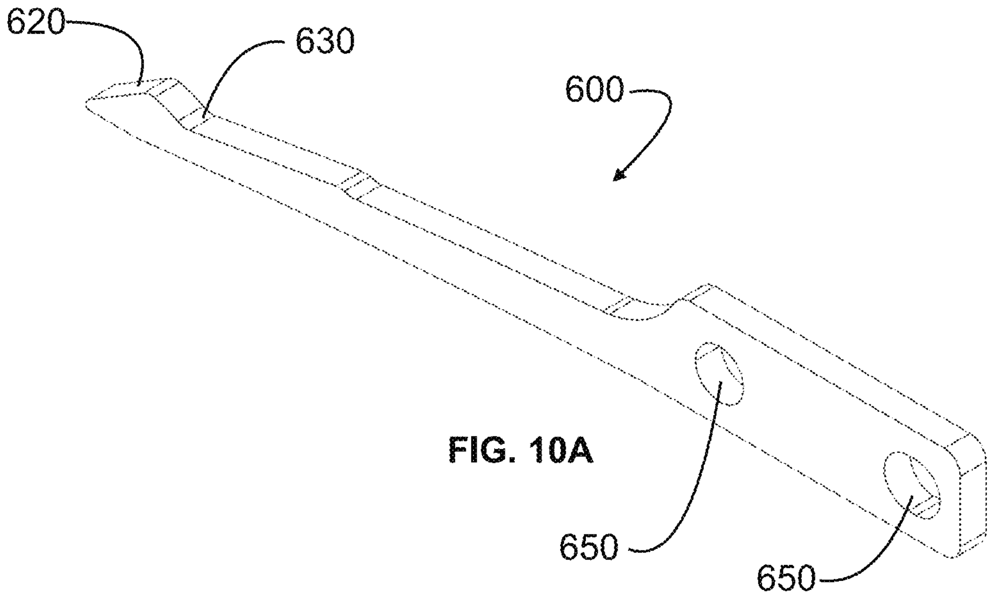
FIG. 10A is a perspective view of a sharp retention arm of the implant inserter assembly of FIG. 1 according to an embodiment.
Figure 10B:
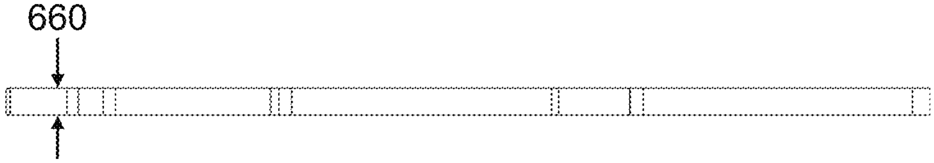
FIG. 10B is a top view of the sharp retention arm of FIG. 10A.
Figure 10C:
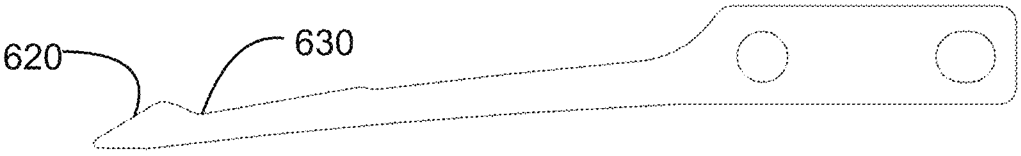
FIG. 10C is a front view of the sharp retention arm of FIG. 10A.

FIG. 10A is a perspective view of a sharp retention arm 600 of an implant inserter assembly 10 according to an embodiment. FIG. 10B is a top view of the sharp retention arm 600 and FIG. 10C is a front view of the sharp retention arm 600. The sharp retention arm 600 may include a retention profile 620, a recessed portion 630, and mounting holes 650.

One or more sharp retention arms 600 may be coupled to the inserter body head 300 so that the one or more sharp retention arms 600 may be moveable relative to each other. The retention profile 620 may be configured as a protruding feature on the sharp retention arm 600. The one or more sharp retention arms 600 may be moveable, relative to each other, along a first direction between the locked configuration and the unlocked configuration. Additionally, the first direction may be transverse to a second direction along which the one or more sharp retention arms 600, in the unlocked configuration, may be withdrawable from the implant assembly 50

The retention profile 620 of the sharp retention arm 600 may be different than the retention profile 520 of the round retention arm 500. The retention profile 620 and the retention profile 520 may be configured so that one or more sharp retention arms 600 and one or more round retention arms 500 engage an implant assembly 50 when the implant assembly 50 is in a single orientation, i.e.: the implant assembly 50 may be load onto the implant inserter assembly 10 in a single orientation. Alternatively, the retention profile 620 and the retention profile 520 may be configured so that one or more sharp retention arms 600 and one or more round retention arms 500 engage an implant assembly 50 when the implant assembly 50 is in a plurality of orientations. The sharp retention arm 600 may include an arm thickness 660 configured to be slidably received in a second arm channel 1550' of a second carriage sideplate 1500.

Figure 11A:
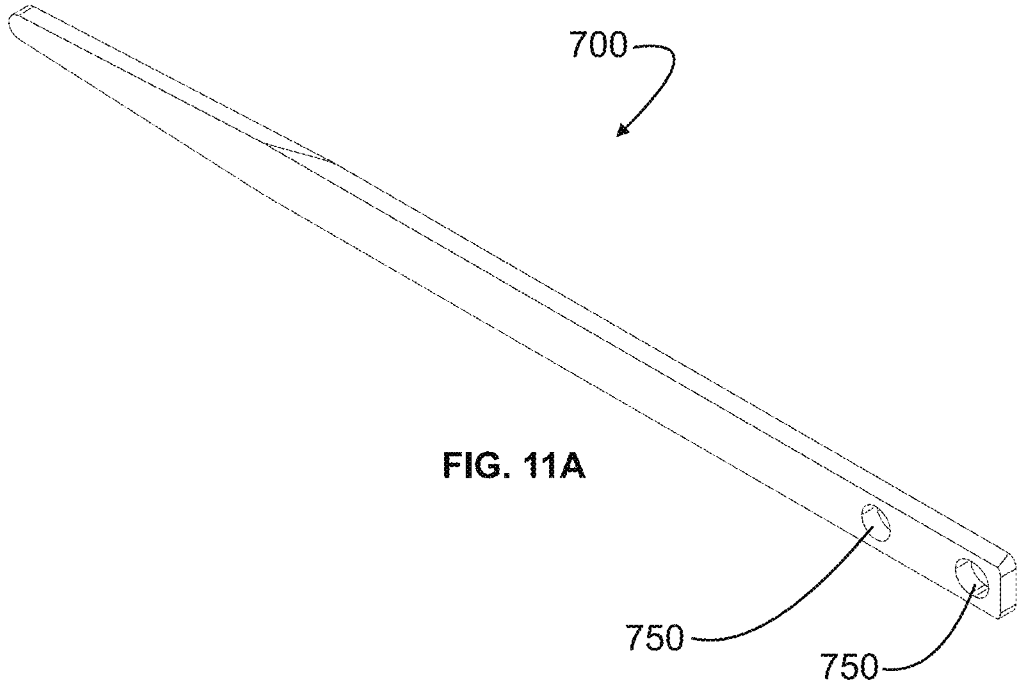
FIG. 11A is a perspective view of a retention wedge of the implant inserter assembly of FIG. 1 according to an embodiment.
Figure 11B:
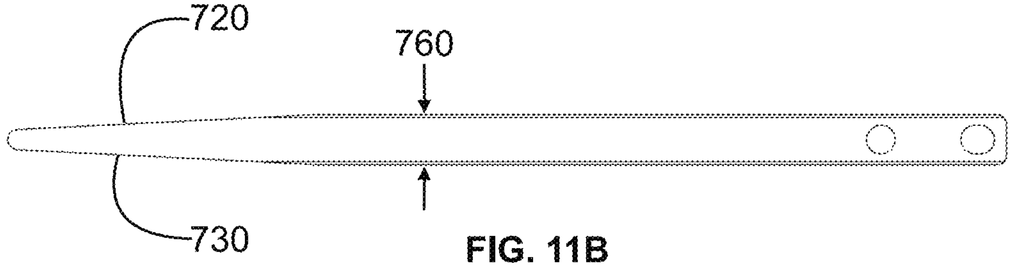
FIG. 11B is a front view of the retention wedge of FIG. 11A.

FIG. 11A is a perspective view of a retention wedge 700 of an implant inserter assembly 10 according to an embodiment. FIG. 11B is a front view of the retention wedge 700. One or more retention wedges 700 may be configured to be slidably received in a first arm channel 1550 and/or a second arm channel 1550'. The one or more retention wedges 700 may further be configured to translate in a proximal-distal direction generally parallel to an axis 170. The one or more retention wedges 700 may be moveable between a locked position, in which a first retention wedge blocks relative motion of a first arm and a second arm from the locked configuration to the unlocked configuration and an unlocked position, in which the first retention wedge does not block relative motion of the first arm and the second arm from the compressed configuration to the unlocked configuration.

The implant inserter assembly 10 and the one or more retention wedges 700 may be configured so that when the one or more retention wedges 700 are in a distal position, retention profiles 520 of one or more round retention arms 500 and retention profiles 620 of one or more sharp retention arms 600 are prevented from deflecting towards the one or more retention wedges 700. The retention wedge 700 may include a first wedge surface 720 configured to slidably engage a first round retention arm 500 and a second wedge surface 730 configured to slidably engage a second round retention arm 500. The retention wedge 700 may include a first wedge surface 720 configured to slidably engage a first sharp retention arm 600 and a second wedge surface 730 configured to slidably engage a second sharp retention arm 600.

The one or more retention wedges 700 may include a wedge width 760 configured to be equal or less than the distance between a first round retention arm 500 and a second round retention arm 500 when the first round retention arm 500 and the second round retention arm 500 are coupled to the inserter body head 300. The one or more retention wedges 700 may include a wedge width 760 configured to be equal or less than the distance between a first sharp retention arm 600 and a second sharp retention arm 600 when the first sharp retention arm 600 and the second sharp retention arm 600 are coupled to the inserter body head 300. One or more retention wedges 700 may include one or more mounting holes 750 configured to securely receive one or more mounting pins 920 of an actuator yoke 900.

In an embodiment, the implant inserter assembly 10 may include two round retention arms 500, two sharp retention arms 600, and two retention wedges 700. The two round retention arms 500 and the first of the two retention wedges 700 may be secured to a first side of the implant inserter assembly 10. The two sharp retention arms 600 and the second of the two retention wedges 700 may be secured to a second side of the implant inserter assembly 10. The two round retention arms 500 may be moveable relative to each other between a locked configuration and a compressed configuration. In the compressed configuration, the two round retention arms 500 may be insertable into a second retention recess 1640 of a plate 1600. Additionally, the two sharp retention arms 600 may be moveable relative to each other between a locked configuration and a compressed configuration. In the compressed configuration, the two sharp retention arms 600 may be insertable into a first retention recess 1630 of the plate 1600.

The implant inserter assembly 10 may be configured so that the retention arm width 20 remains generally unchanged when the two round retention arms 500 and/or the two sharp retention arms 600 are in the locked configuration relative to when the two round retention arms 500 and/or the two sharp retention arms 600 are in the compressed configuration.

Compression of the two round retention arms 500 towards each other may define a first direction. Compression of the two sharp retention arms 600 may also occur in the first direction. The first retention recess 1630 and/or the second retention recess 1640 may extend parallel to the first direction.

Figure 12A:
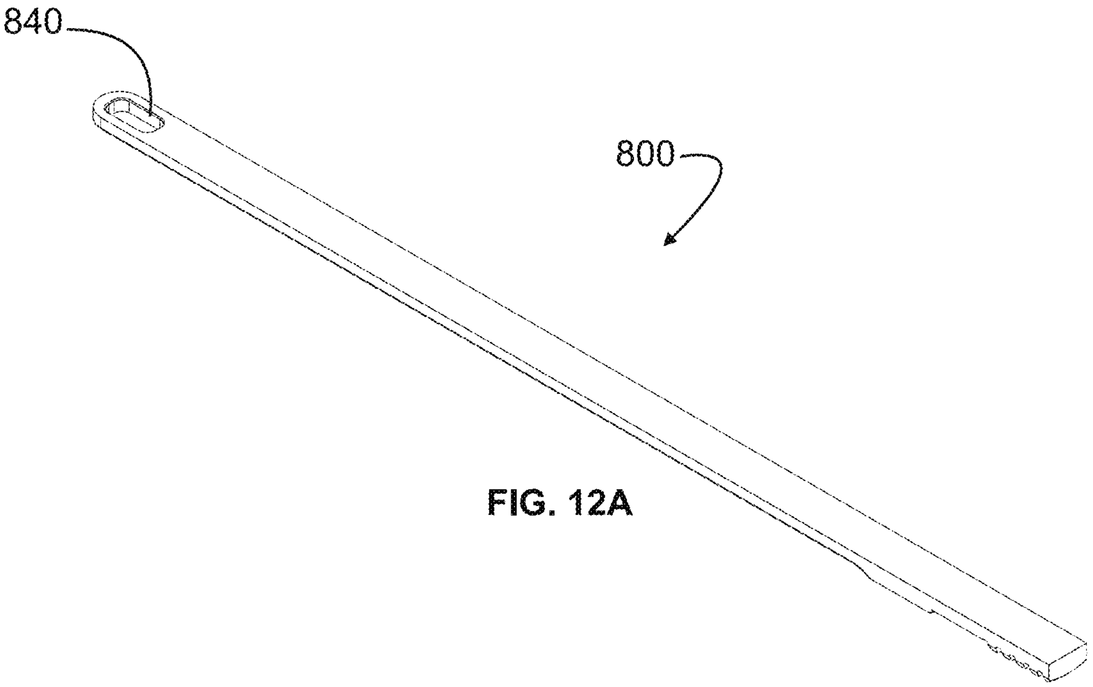
FIG. 12A is a perspective view of a wedge actuator of the implant inserter assembly of FIG. 1 according to an embodiment.
Figure 12B:
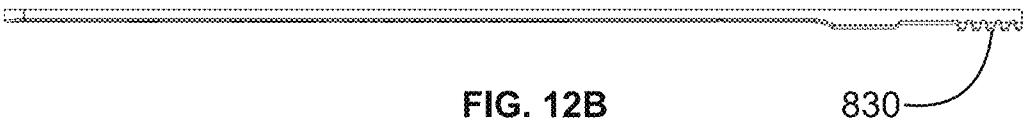
FIG. 12B is a top view of the wedge actuator of FIG. 12A.
Figure 12C:
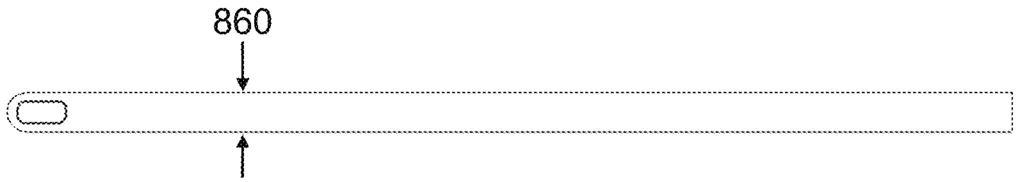
FIG. 12C is a front view of the wedge actuator of FIG. 12A.

FIG. 12A is a perspective view of a wedge actuator 800 of an implant inserter assembly 10 according to an embodiment. FIG. 12B is a top view of the wedge actuator 800 and FIG. 12C is a front view of the wedge actuator 800. The wedge actuator 800 may be configured to translate linearly in a direction generally parallel to the axis 170. The wedge actuator 800 may be configured to so that the position of the wedge actuator 800 may be adjusted at the proximal end of the implant inserter assembly 10. The wedge actuator 800 may include a threaded portion 830, a linkage portion 840, and an actuator width 860. The threaded portion 830 may be configured to threadably engage a threaded portion 1130 of a lock ring 1100 wherein rotation about an axis of the lock ring 1100 may result in linear translation of the wedge actuator 800. The linkage portion 840 may be configured to couple to a linkage portion 940 of an actuator yoke 900 wherein linear translation of the wedge actuator 800 may result in linear translation of the actuator yoke 900. The actuator width 860 may be configured to slidably engage a bottom channel 210 of an inserter body bottom 200.

Figure 13B:
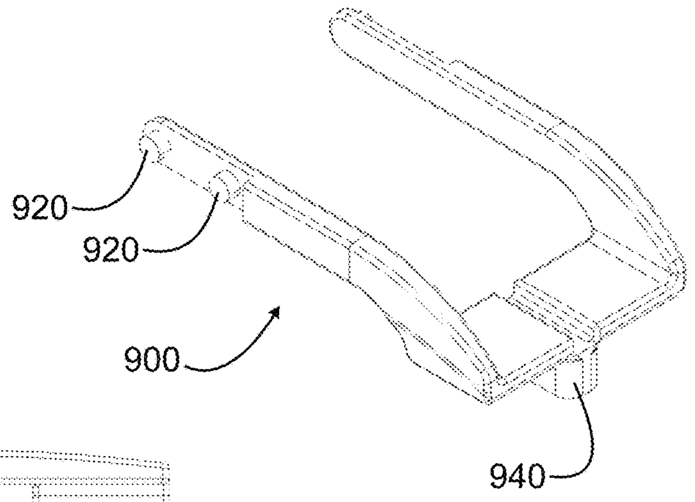
FIG. 13B is a perspective view of the actuator yoke of FIG. 13A.
Figure 13A:
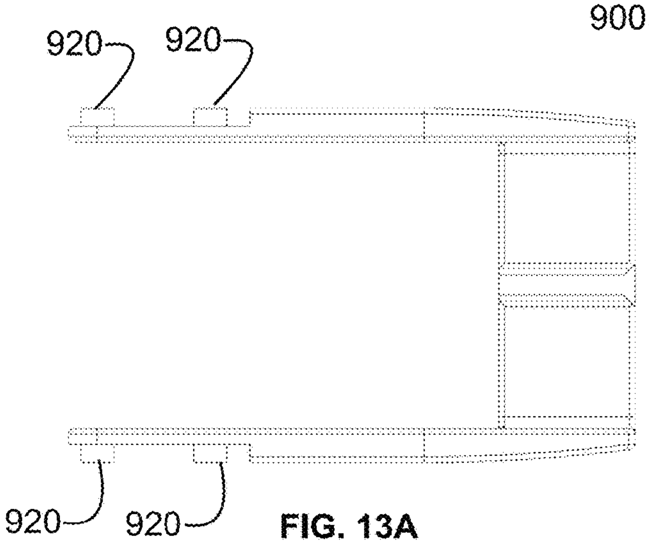
FIG. 13A is a top view of an actuator yoke of the implant inserter assembly of FIG. 1 according to an embodiment.
Figure 13C:
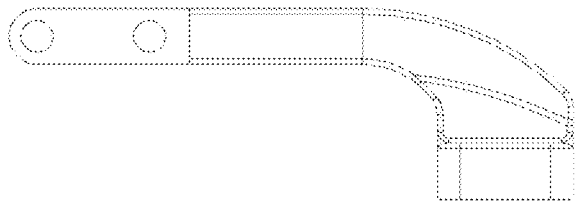
FIG. 13C is a front view of the actuator yoke of FIG. 13A.
Figure 13D:
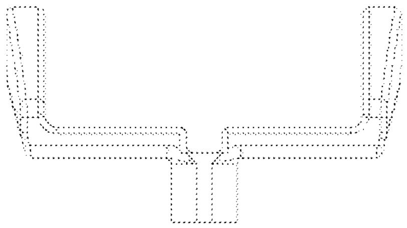
FIG. 13D is a right-side view of the actuator yoke of FIG. 13A.

FIG. 13A is a top view of an actuator yoke 900 of an implant inserter assembly 10 according to an embodiment. FIG. 13B is a perspective view of the actuator yoke 900, FIG. 13C is a front view of the actuator yoke 900, and FIG. 13D is a right-side view of the actuator yoke 900. The actuator yoke 900 may be configured to transfer linear translation of the wedge actuator 800 to one or more retention wedges 700. The actuator yoke may include one or more mounting pins 920 and a linkage portion 940. The one or more mounting pins 920 may be configured to securely engage one or more mounting holes 750 of one or more retention wedges 700. The linkage portion 940 may be configured to couple to a linkage portion 840 of a wedge actuator 800 wherein linear translation of the wedge actuator 800 may result in linear translation of the actuator yoke 900.

Figure 14A:
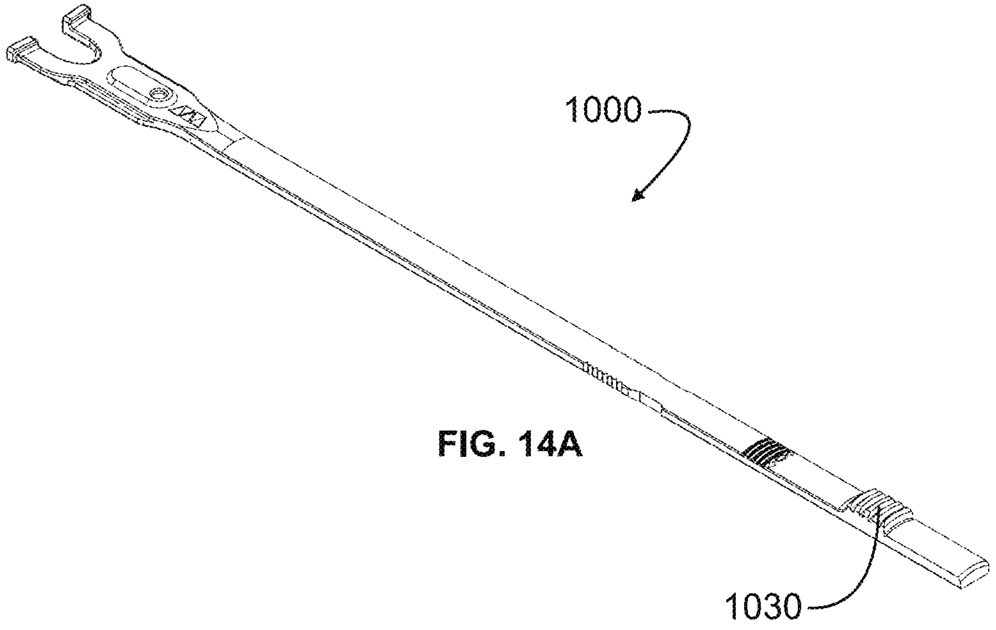
FIG. 14A is a perspective view of a depth-stop of the implant inserter assembly of FIG. 1 according to an embodiment.
Figure 14B:
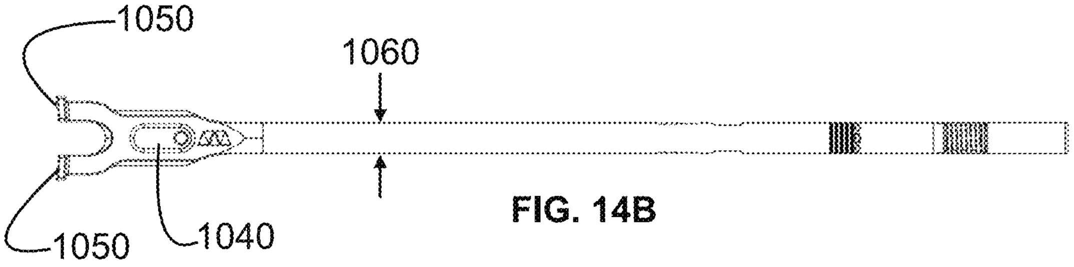
FIG. 14B is a top view of the depth-stop of FIG. 14A.
Figure 14C:
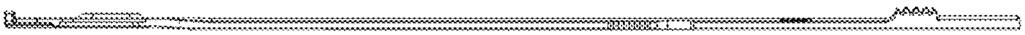
FIG. 14C is a front view of depth-stop of FIG. 14A.

FIG. 14A is a perspective view of a depth-stop 1000 of an implant inserter assembly 10 according to an embodiment. FIG. 14B is a top view of the depth-stop 1000 and FIG. 14C is a front view of the depth-stop 1000. The depth-stop 1000 may be configured to translate linearly in a direction generally parallel to the axis 170. The depth-stop 1000 may be configured to so that the position of the depth-stop 1000 may be adjusted at the proximal end of the implant inserter assembly 10. The depth-stop 1000 may include a threaded portion 1030, a locating slot 1040, one or more stop faces 1050, and a depth-stop width 1060. The threaded portion 1030 may be configured to threadably engage a threaded portion 1230 of a depth ring 1200 wherein rotation about an axis of the depth ring 1200 may result in linear translation of the depth-stop 1000. The depth-stop width 1060 may be configured to slidably engage a top channel 110 of an inserter body top 100.

Figure 15A:
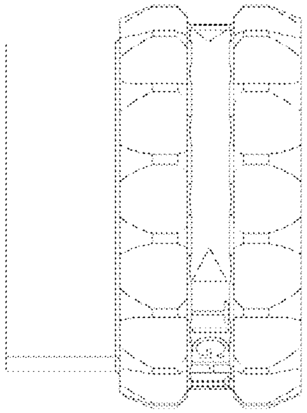
FIG. 15A is a top view of a lock ring of the implant inserter assembly of FIG. 1 according to an embodiment.
Figure 15B:
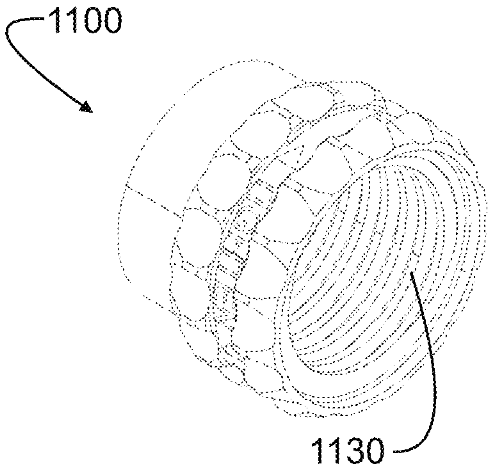
FIG. 15B is a perspective view of the lock ring of FIG. 15A.
Figure 15C:
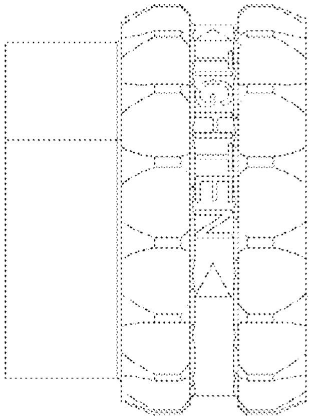
FIG. 15C is a front view of the lock ring of FIG. 15A.
Figure 15D:
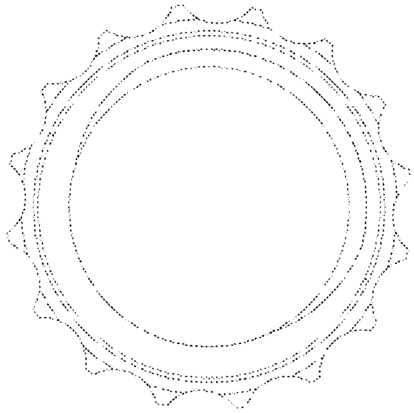
FIG. 15D is a right-side view of the lock ring of FIG. 15A.

FIG. 15A is a top view of a lock ring 1100 of an implant inserter assembly 10 according to an embodiment. FIG. 15B is a perspective view of the lock ring 1100, FIG. 15C is a front view of the lock ring 1100, and FIG. 15D is a right-side view of the lock ring 1100. The lock ring 1100 may include a threaded portion 1130 and may be configured to threadably engage a wedge actuator 800 wherein rotation about an axis of the lock ring 1100 may result in linear translation of the wedge actuator 800.

Figure 16A:
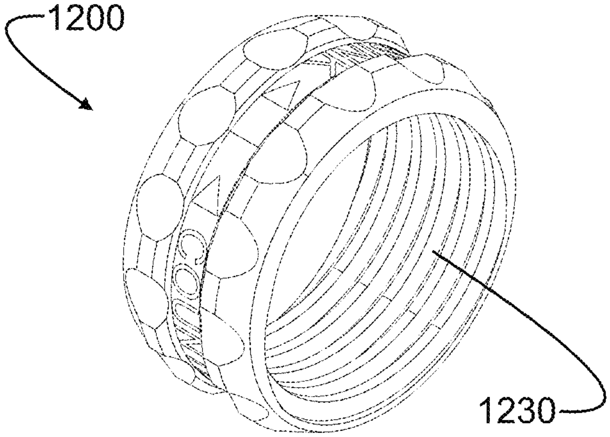
FIG. 16A is a perspective view of a depth ring of the implant inserter assembly of FIG. 1 according to an embodiment.
Figure 16B:
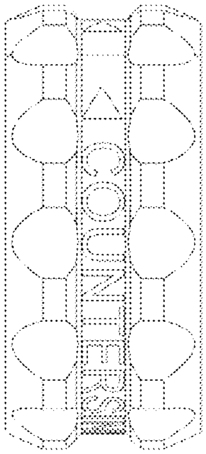
FIG. 16B is a top view of the depth ring of FIG. 16A.
Figure 16C:
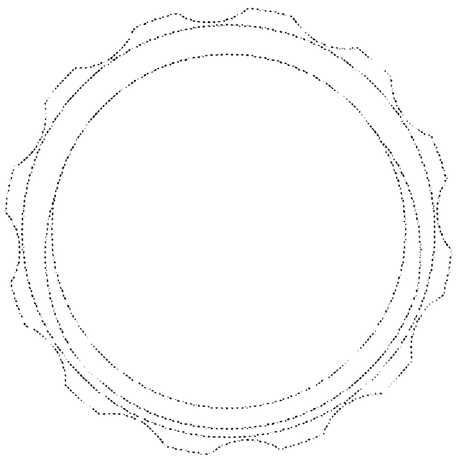
FIG. 16C is a front view of depth ring of FIG. 16A.

FIG. 16A is a perspective view of a depth ring 1200 of an implant inserter assembly 10 according to an embodiment. FIG. 16B is a top view of the depth ring 1200, and FIG. 16C is a front view of the depth ring 1200. The depth ring 1200 may include a threaded portion 1230 and may be configured to threadably engage a depth-stop 1000 wherein rotation about an axis of the depth ring 1200 may result in linear translation of the depth-stop 1000.

Figure 17A:
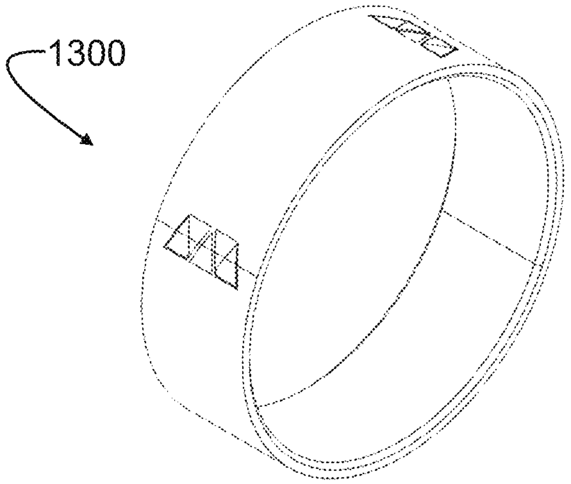
FIG. 17A is a perspective view of a slip ring of the implant inserter assembly of FIG. 1 according to an embodiment.
Figure 17B:
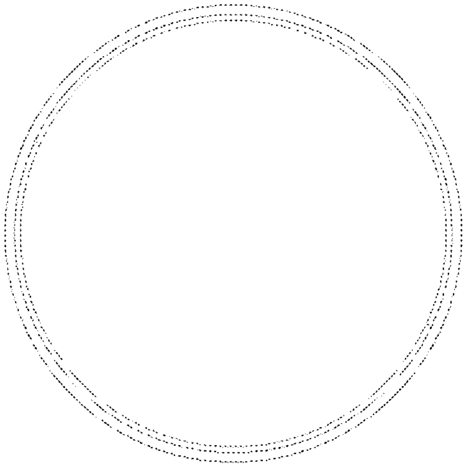
FIG. 17B is a front view of slip ring of FIG. 17A.

FIG. 17A is a perspective view of a slip ring 1300 of an implant inserter assembly 10 according to an embodiment. FIG. 17B is a front view of slip ring 1300. The slip ring 1300 may be configured as a spacer between the lock ring 1100 and the depth ring 1200.

Figure 18A:
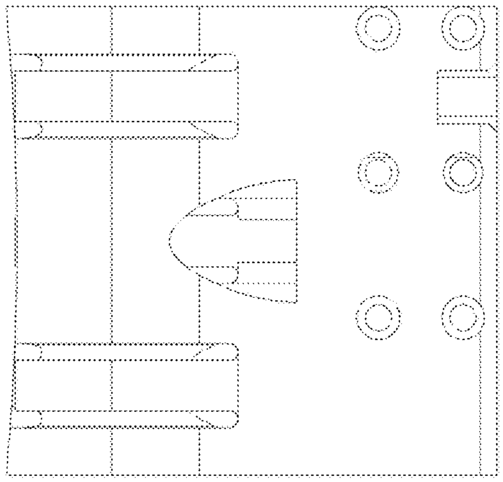
FIG. 18A is a top view of a spike carriage of the spike carriage assembly of FIG. 1 according to an embodiment.
Figure 18B:
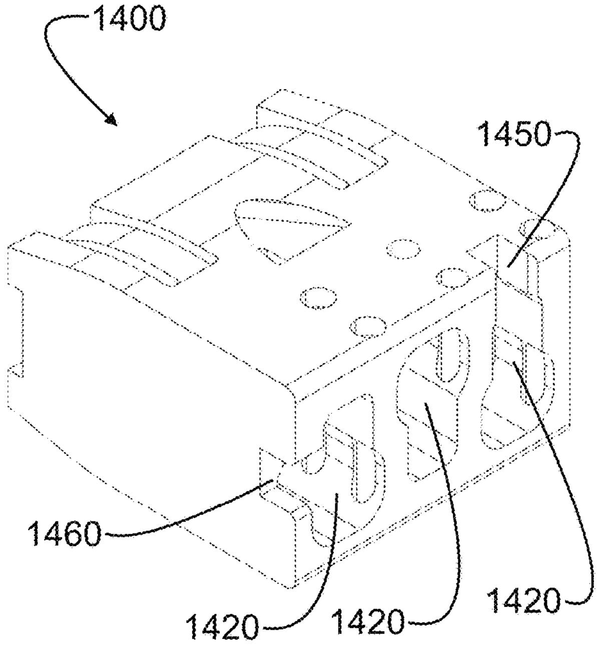
FIG. 18B is a perspective view of the spike carriage of FIG. 18A.
Figure 18C:
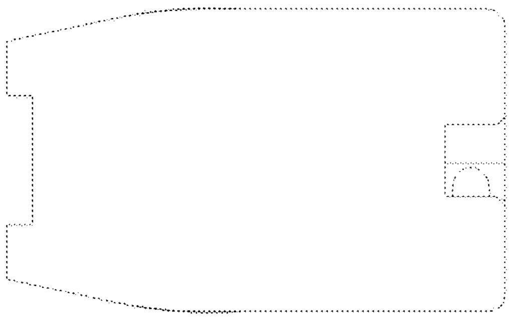
FIG. 18C is a front view of the spike carriage of FIG. 18A.
Figure 18D:
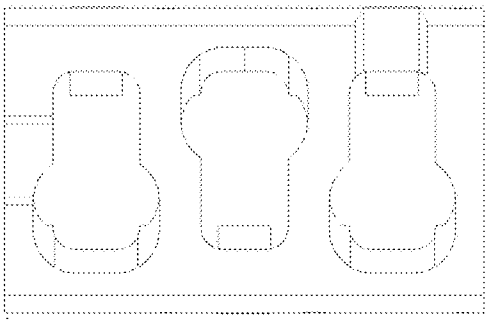
FIG. 18D is a right-side view of the spike carriage of FIG. 18A.

FIG. 18A is a top view of a spike carriage 1400 of a spike carriage assembly 60 according to an embodiment. FIG. 18B is a perspective view of the spike carriage 1400, FIG. 18C is a front view of the spike carriage 1400, and FIG. 18D is a right-side view of the spike carriage 1400. The spike carriage 1400 may include one or more guide channels 1420 configured to retain one or more superior fasteners (not shown) and/or one or more inferior fasteners (not shown). The spike carriage 1400 may include a first locating notch 1450 and a second locating notch 1460. The first locating notch 1450 may be configured to engage the first locating feature 350 of the inserter body head 300 and the second locating notch 1460 may be configured to engage the second locating feature 360 of the inserter body head 300. Additionally, the first locating feature 350, the second locating feature 360, the first locating notch 1450, and the second locating notch 1460 may be configured so that a spike carriage assembly 60 may engage the inserter body head 300 in a single orientation. Alternatively, the first locating feature 350, the second locating feature 360, the first locating notch 1450, and the second locating notch 1460 may be configured so that the spike carriage assembly 60 may engage the inserter body head 300 in a plurality of orientations.

FIG. 19A is a top view of a carriage sideplate 1500 of a spike carriage assembly 60 according to an embodiment. FIG. 19B is a perspective view of the carriage sideplate 1500, FIG. 19C is a front view of the carriage sideplate 1500, and FIG. 19D is a right-side view of the carriage sideplate 1500. One or more carriage sideplates 1500 may be configured to securely engage a spike carriage 1400 and may facilitate retention of a spike carriage assembly 60 on the implant inserter assembly 10. The one or more carriage sideplates may each include a first arm channel 1550 and/or a second arm channel 1550' each having and an arm channel depth 1560. The spike carriage assembly 60 may be configured with a first arm channel 1550 on a first side and a second arm channel 1550' on a second side. The first arm channel 1550 on the first side may be configured to slidably receive one or more round retention arms 500. The second arm channel 1550' on the second side may be configured to slidably receive one or more sharp retention arms 600. The arm channel depth 1560 may be configured to be greater than or equal to the arm thickness 560 of the round retention arm 500, the arm thickness 660 of the sharp retention arm, and/or the wedge width 760 of the retention wedge 700.

Figure 20A:
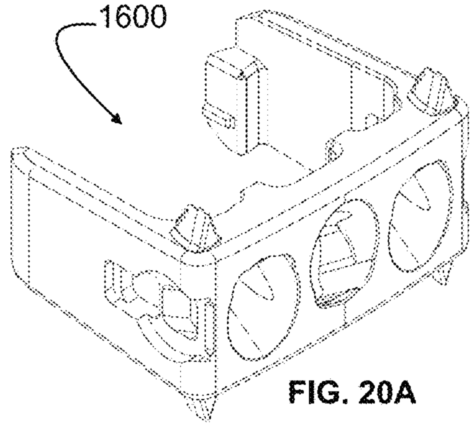
FIG. 20A is a perspective view of a plate of the implant assembly of FIG. 1 according to an embodiment.
Figure 20B:
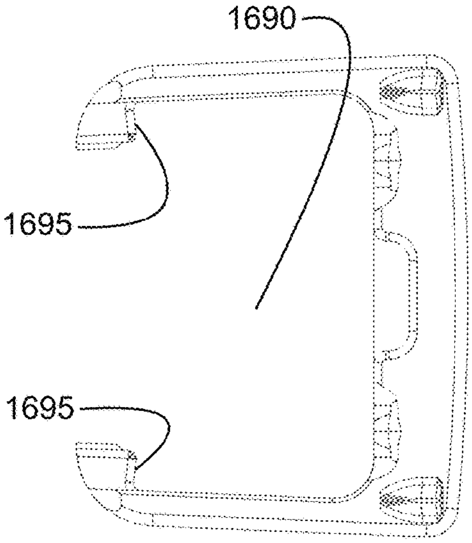
FIG. 20B is a top view of the plate of FIG. 20A.
Figure 20C:
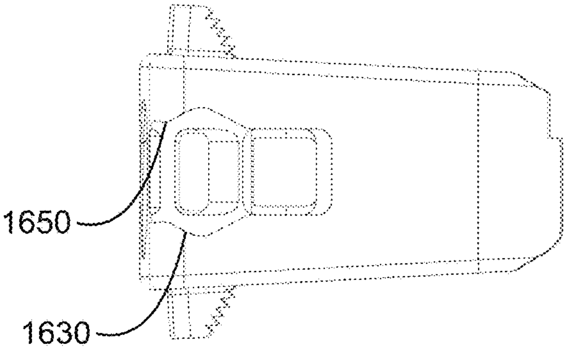
FIG. 20C is a back view of the plate of FIG. 20A.
Figure 20D:
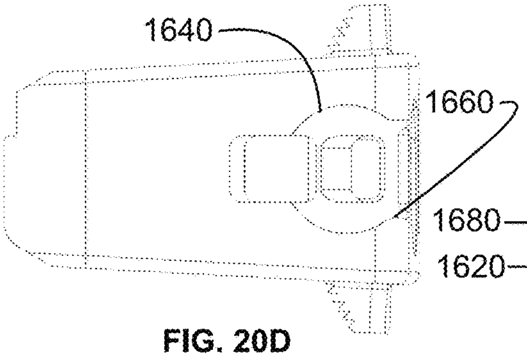
FIG. 20D is a front view of the plate of FIG. 20A.
Figure 20E:
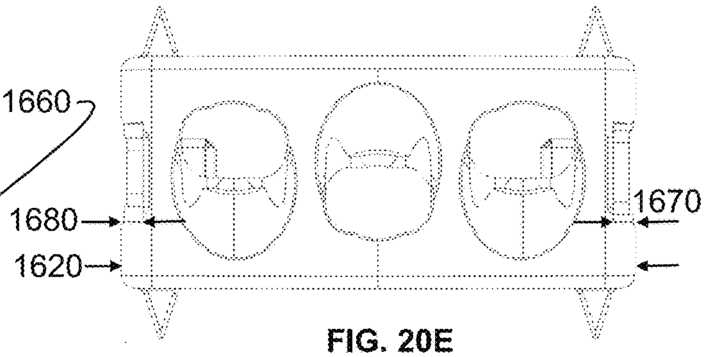
FIG. 20E is a right-side view of the plate of FIG. 20A.

FIG. 20A is a perspective view of a plate 1600 of an implant assembly 50 according to an embodiment. FIG. 20B is a top view of the plate 1600, FIG. 20C is a back view of the plate 1600, FIG. 20D is a front view of the plate 1600, and FIG. 20E is a right-side view of the plate 1600. The plate 1600 may be configured to be removably engaged by the implant inserter assembly 10. The plate 1600 may include a first retention recess 1630, a second retention recess 1640, a first retention recess lead-in 1650, and a second retention recess lead-in 1660. When the plate 1600 is engaged by the implant inserter assembly 10, the first retention recess 1630 and the second retention recess 1640 may each extend parallel to the axis 170.

The first retention recess 1630 may be configured to receive the retention profile 520 of the round retention arm 500. Additionally, the second retention recess 1640 may be configured to receive the retention profile 620 of the second retention arm 600.

The first retention recess 1630 may be configured to generally match the retention profile 620 of the sharp retention arm 600 and the second retention recess 1640 may be configured to generally match the retention profile 520 of the round retention arm 500. Additionally, the first retention recess lead-in 1650 may be configured to engage the recessed portion 630 of the sharp retention arm 600 and the second retention recess lead-in 1660 may be configured to engage the recessed portion 530 of the round retention arm 500.

The plate 1600 may include a plate width 1620, a first retention recess depth 1670, and a second retention recess depth 1680. The first retention recess depth 1670 may be generally equal to the arm thickness 660 of the sharp retention arm 600 and the second retention recess depth 1680 may be generally equal to the arm thickness 560 of the round retention arm 500. Alternatively, the first retention recess depth 1670 may be greater than the arm thickness 660 of the sharp retention arm 600 and the second retention recess depth 1680 may be greater than the arm thickness 560 of the round retention arm 500. Alternatively, the first retention recess depth 1670 may be less than the arm thickness 660 of the sharp retention arm 600 and the second retention recess depth 1680 may be less than the arm thickness 560 of the round retention arm 500.

The plate 1600 may include a central portion 1690 and one or more retention features 1695. The central portion 1690 may be configured to receive a body 1700. The implant assembly 50 may include a plate 1600 and a body 1700. Additionally, the implant assembly 50 may be configured in a range of widths (12 mm to 20 mm), heights (5 mm to 12 mm), and lordotic angles (0° to) 10°. The implant inserter assembly 10 may be configured in a range of widths wherein a retention arm width 20 may be generally equal to the implant assembly 50 width. Alternatively, the implant inserter assembly 10 may be configured in a single width wherein the first retention recess depth 1670 and the second retention recess depth 1680 are configured differently for different implant assembly 50 widths such that the first retention recess depth 1670 plus the second retention recess depth 1680 plus the retention arm width 20 generally equals the plate width 1620.

Figure 21B:
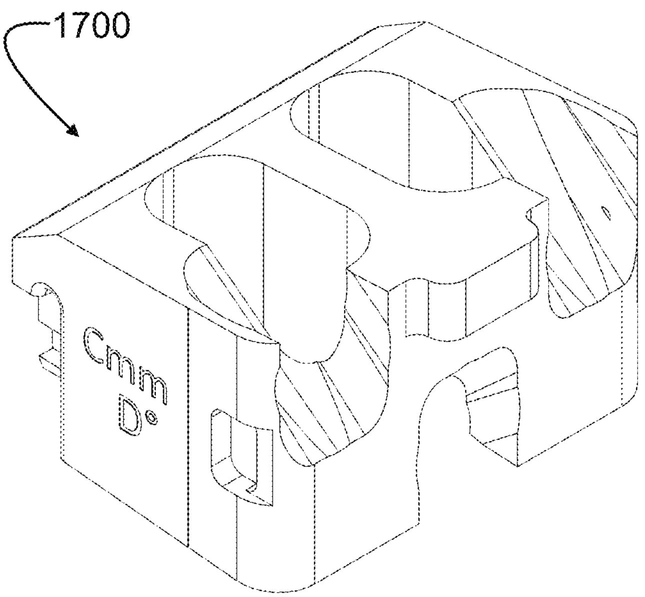
FIG. 21B is a perspective view of the body of FIG. 21A.
Figure 21A:
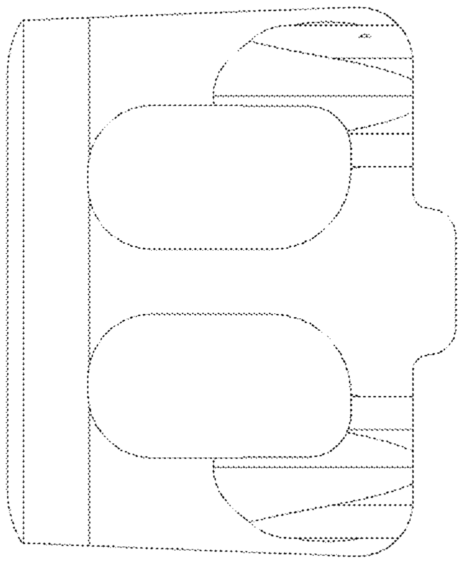
FIG. 21A is a top view of a body of the implant assembly of FIG. 1 according to an embodiment.
Figure 21C:
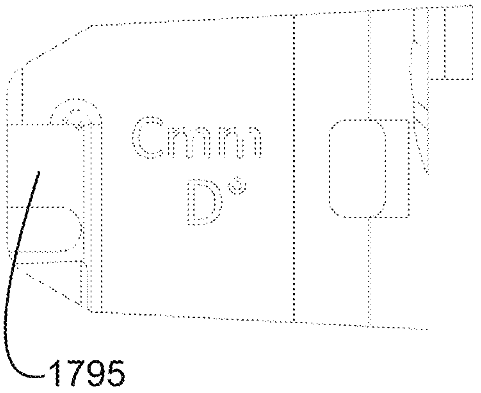
FIG. 21C is a front view of the body of FIG. 21A.
Figure 21D:
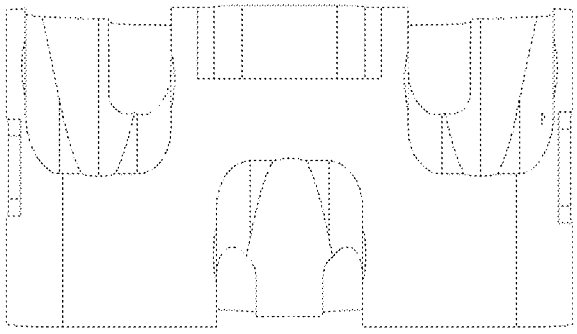
FIG. 21D is a right-side view of the body of FIG. 21A.

FIG. 21A is a top view of a body 1700 of an implant assembly 50 according to an embodiment. FIG. 21B is a perspective view of the body 1700, FIG. 21C is a front view of the body 1700, and FIG. 21D is a right-side view of the body. The body 1700 may include one or more retention features 1795. The one or more retention features 1695 of the plate 1600 may be configured to securably engage the body 1700. The one or more retention features 1695 may be configured to engage one or more retention features 1795 of the body 1700.

Figure 22A:
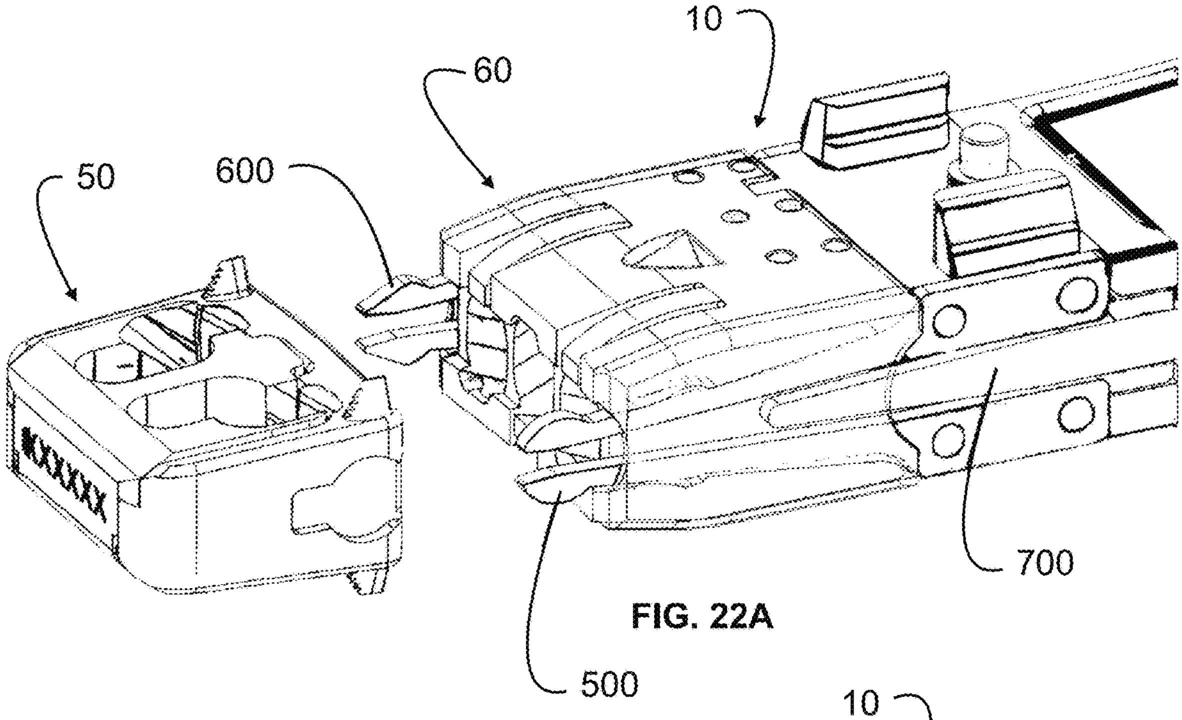
FIG. 22A is a perspective view of the implant inserter assembly connected to the spike carriage assembly of FIG. 1 and not connected to the implant assembly of FIG. 1.
Figure 22B:
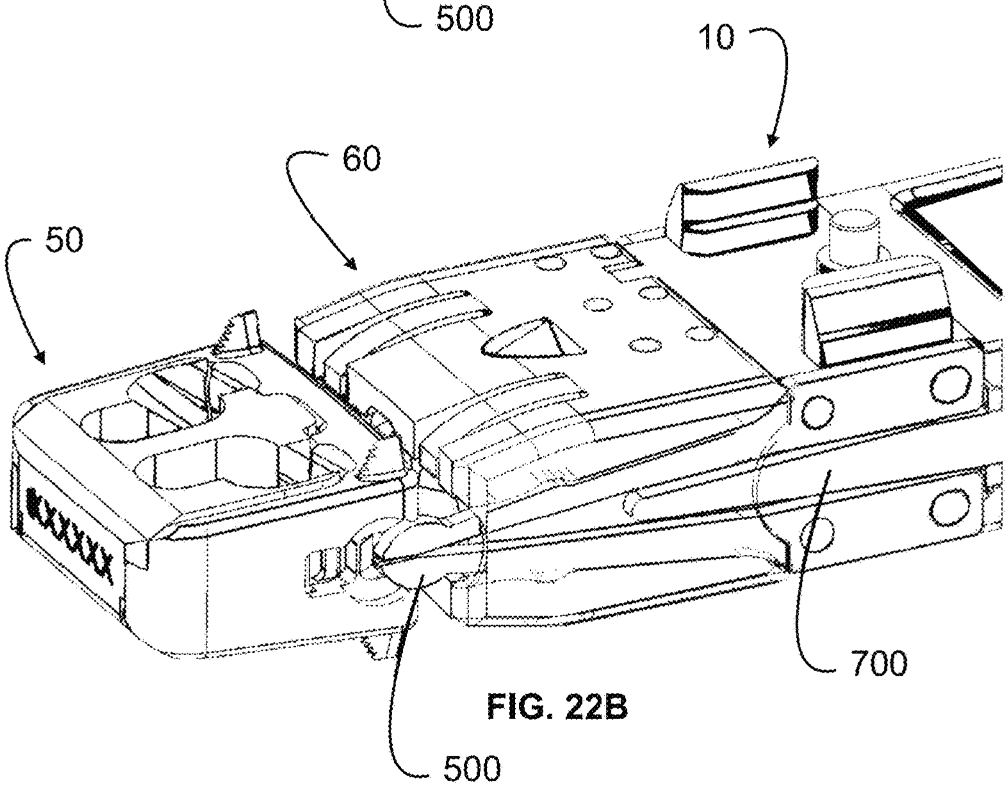
FIG. 22B is a perspective view of the implant inserter assembly connected to the spike carriage assembly of FIG. 1 and partially connected to the implant assembly of FIG. 1.
Figure 22C:
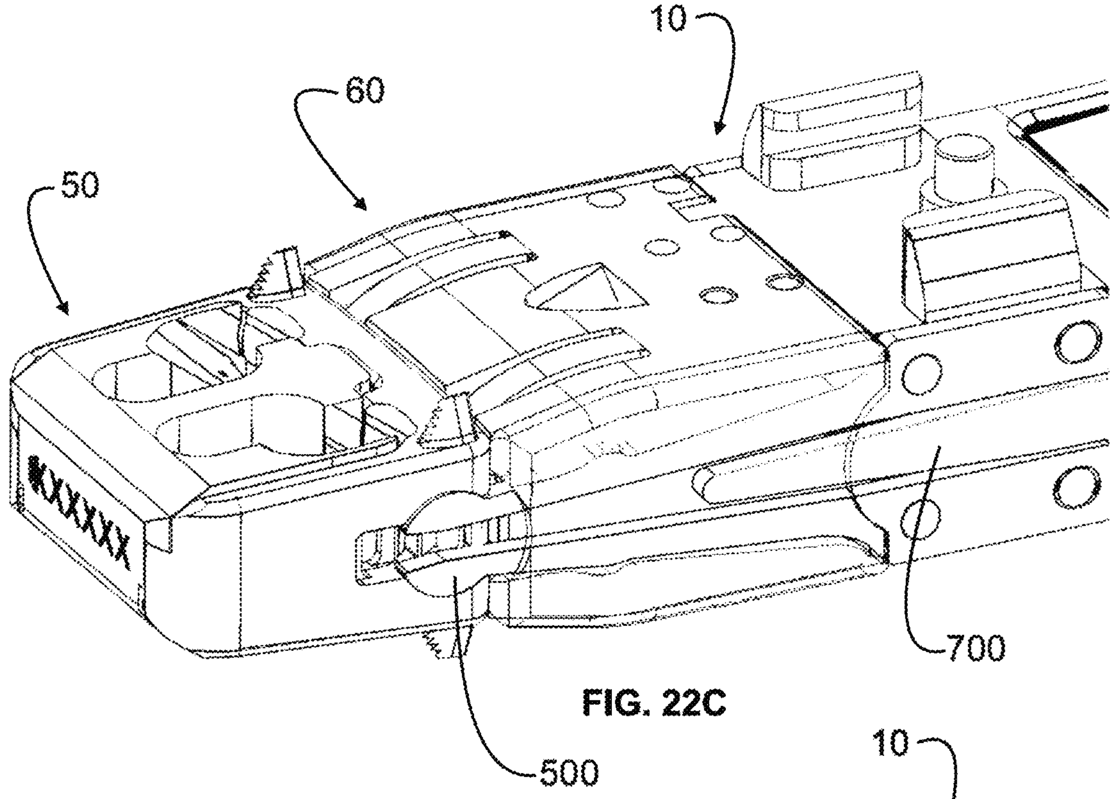
FIG. 22C is a perspective view of the implant inserter assembly, the spike carriage assembly and the implant assembly of FIG. 1 in a connected state.
Figure 22D:
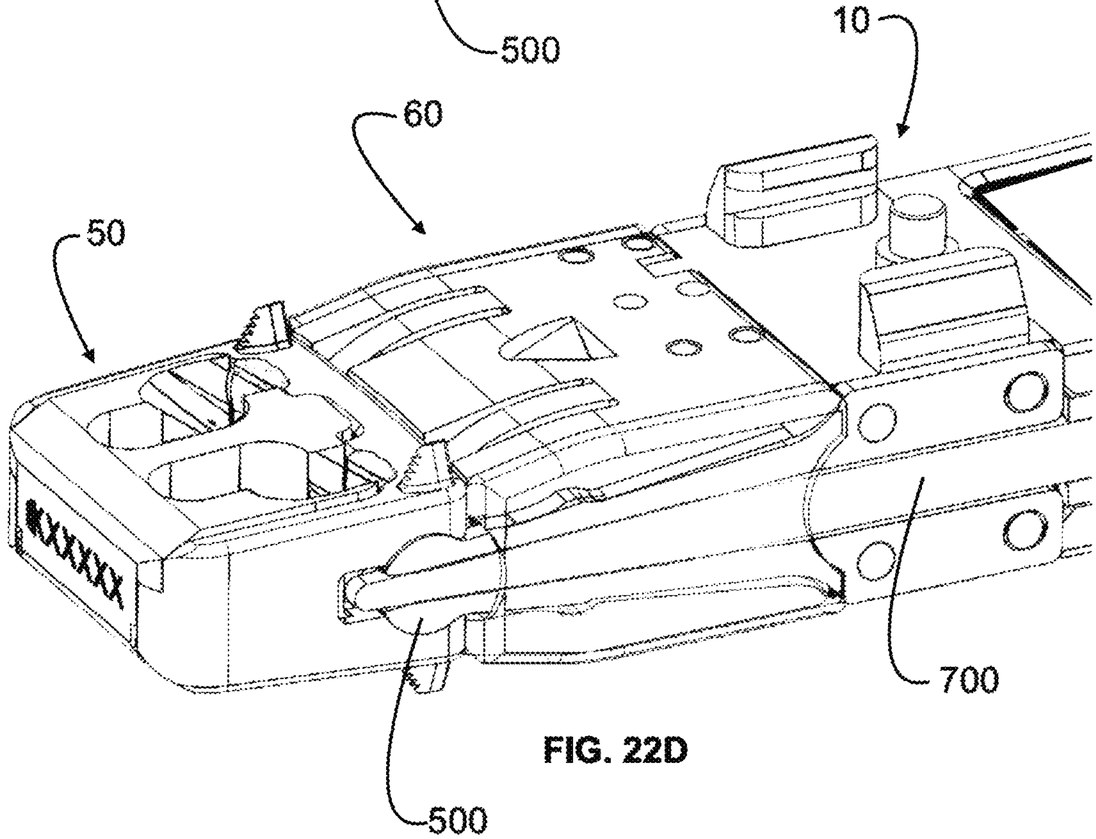
FIG. 22D is a perspective view of the implant inserter assembly, the spike carriage assembly and the implant assembly of FIG. 1 in a connected state.

FIG. 22A though FIG. 22D illustrate one exemplary method for engaging an implant assembly 50 using an implant inserter assembly 10 according to an embodiment. The method for engaging the implant assembly 50 using an implant inserter assembly 10 according to an embodiment may include the following steps (a depth-stop 1000 is not shown for clarity):

1. Two retention wedges 700 may be in a retracted position, two round retention arms 500 and two sharp retention arm 600 may be in a non-compressed state, and an implant assembly 50 may be oriented so that the first retention recesses 1630 are aligned with the sharp retention arms 600 and the second retention recesses 1640 are aligned with the round retention arms 500.
2. The implant assembly 50 may be advanced toward the implant inserter assembly 10. A first retention recess lead-in 1650 may compresses the two sharp retention arms 600 into a compressed configuration and a second retention recess lead-in 1660 compresses the two round retention arms 500 into a compressed configuration.
3. When the implant assembly 50 may be fully engaged, the first retention recesses 1630 allow the two sharp retention arms 600 to return to a non-compressed state and the second retention recesses 1640 allow the two round retention arms 500 to return to a non-compressed state.
4. The two retention wedges 700 may be advanced to a locked configuration and may prevent compression of the two sharp retention arms 600 and the two round retention arms 500. The first retention recess lead-in 1650 may prevent the retention profiles 620 of the two sharp retention arms from disengaging from the implant assembly 50. The second retention recess lead-in 1660 may prevent the retention profiles 520 of the two round retention arms 500 from disengaging from the implant assembly 50.
5. After placement of the implant assembly 50 within an intervertebral space, the two retention wedges may be retracted, allowing compression of the two sharp retention arms 600 and the two round retention arms 500 as the implant inserter assembly 10 may be withdrawn from the implant assembly 50.

In an exemplary method for engaging an implant assembly 50 and a spike carriage assembly 60 using an implant inserter assembly 10, the above method may also include the following steps:

1. Orient a spike carriage assembly 60 so that a first locating notch 1450 of a spike carriage 1400 may correspond to a first locating feature 350 of the inserter body head 300 and a second locating notch 1460 of the spike carriage 1400 may correspond to a second locating feature 360 of the inserter body head 300.
2. Slide the spike carriage assembly 60 over the two sharp retention arms 600 and the two round retention arms 500 until fully engaged.
3. Perform steps 1 through 5 above to engage an implant assembly 50.

Those of skill in the art will recognize that this is only one of many potential methods that may be used for engaging an implant using an implant inserter assembly. Further, the method set forth in FIG. 22A through FIG. 22D may be employed to use an implant inserter assembly to engage other implants besides those specifically disclosed herein.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The phrases "generally parallel" and "generally perpendicular" refer to structures that are within 30° parallelism or perpendicularity relative to each other, respectively. Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the disclosure.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure without departing from its spirit and scope.

What is claimed is:

1. A system for inserting an implant into an intervertebral space, the system comprising:

an implant:

an implant inserter, comprising:

a first arm;

a second arm; and a first retention member positioned between the first arm and the second arm;

wherein the first arm and the second arm are moveable, relative to each other, between:

a locked configuration in which the first arm and the second arm are spaced apart such that the first arm and the second arm are locked in place relative to the implant; and a compressed configuration, in which the first arm and the second arm are less spaced apart such that the first arm and the second arm are withdrawable from the implant;

wherein the first retention member is moveable between:

a locked position in which the first retention member blocks relative motion of the first arm and the second arm from the locked configuration to the compressed configuration; and an unlocked position in which the first retention member does not block relative motion of the first arm and the second arm from the locked configuration to the compressed configuration wherein the implant includes a first recess configured to receive a first protruding feature on the first arm and a second recess configured to receive a second protruding feature on the second arm.

2. The system of claim 1, wherein the implant inserter further comprises:

a third arm;

a fourth arm; and a second retention member;

wherein the third arm and the fourth arm are moveable, relative to each other, between:

a locked configuration in which the third arm and the fourth arm are spaced apart such that the third arm and the fourth arm are locked in place relative to the implant; and a compressed configuration, in which the third arm and the fourth arm are less spaced apart such that the third arm and the fourth arm are withdrawable from the implant;

wherein the second retention member is moveable between:

a locked position in which the second retention member blocks relative motion of the third arm and the fourth arm from the locked configuration to the compressed configuration; and an unlocked position in which the second retention member does not block relative motion of the third arm and the fourth arm from the locked configuration to the compressed configuration.

3. The system of claim 2, wherein the implant further comprises:

a third recess configured to receive a third protruding feature on the third arm; and a fourth recess configured to receive a fourth protruding feature on the fourth arm.

4. The system of claim 2, wherein:

the implant further comprises an implant width measured at a widest portion of the implant; and the implant inserter further comprises:

a first distance between the first arm and the third arm in the locked configuration; and a second distance between the first arm and the third arm in the compressed configuration;

wherein the first distance and the second distance are less than or equal to the implant width.

5. The system of claim 2, wherein a first distance between the first arm and the third arm and a second distance between the second arm and the fourth arm are generally equal in the locked configuration as in the compressed configuration.

6. The system of claim 1, wherein:

the first arm and the second arm are further moveable, relative to each other, along a first direction between the locked configuration and the compressed configuration; and the first direction is transverse to a second direction along which the first arm and the second arm are withdrawable from the implant in the compressed configuration.

7. The system of claim 6, further comprising the implant; wherein the implant comprises:

a first recess extending parallel to the first direction to receive a first protruding feature on the first arm; and a second recess extending parallel to the first direction to receive a second protruding feature on the second arm.

8. A system for inserting an implant into an intervertebral space, the system comprising:

an implant; and an implant inserter, comprising:

a first arm;

a second arm;

a third arm;

a fourth arm;

a first retention member; and a second retention member;

wherein the first arm and the second arm are moveable, relative to each other, and the third arm and the fourth arm are moveable, relative to each other, between:

a locked configuration in which the first arm is spaced apart from the second arm and the third arm is spaced apart from the fourth arm, such that the first arm, the second arm, the third arm, and the fourth arm are locked in place relative to the implant, the first arm and the second arm are spaced apart a first distance, the first retention member prevents relative movement of the first arm and the second arm, the third arm and the fourth arm are spaced apart the first distance, and the second retention member prevents relative movement of the third arm and the fourth arm;

a compressible configuration in which the first arm and the second arm are spaced apart the first distance and the first retention member does not prevent relative movement of the first arm and the second arm, the third arm and the fourth arm are spaced apart the first distance and the second retention member does not prevent relative movement of the third arm and the fourth arm; and a compressed configuration, in which the first arm is less spaced apart from the second arm and the third arm is less spaced apart from the fourth arm, such that the first arm, the second arm, the third arm, and the fourth arm are withdrawable from the implant, the first arm and the second arm are spaced apart a second distance, the third arm and the fourth arm are spaced apart the second distance, and the second distance is less than the first distance.

9. The system of claim 8, wherein the implant comprises:

a first recess configured to receive a first protruding feature on the first arm;

a second recess configured to receive a second protruding feature on the second arm;

a third recess configured to receive a third protruding feature on the third arm; and a fourth recess configured to receive a fourth protruding feature on the fourth arm.

10. The system of claim 8, wherein:

the first arm and the second arm are further moveable, relative to each other, along a first direction between the locked configuration and the compressed configuration;

the third arm and the fourth arm are further moveable, relative to each other, along the first direction between the locked configuration and the compressed configuration; and the first direction is transverse to a second direction along which the first arm, the second arm, the third arm, and the fourth arm are withdrawable from the implant in the compressed configuration.

11. The system of claim 10, wherein the implant comprises:

a first recess extending parallel to the first direction to receive a first protruding feature on the first arm;

a second recess extending parallel to the first direction to receive a second protruding feature on the second arm;

a third recess extending parallel to the first direction to receive a third protruding feature on the third arm; and a fourth recess extending parallel to the first direction to receive a fourth protruding feature on the second arm.

12. The system of claim 8, wherein the implant inserter further comprises:

a first retention member; and a second retention member;

wherein the first retention member and the second retention member are moveable between:

a locked position in which the first retention member blocks relative motion of the first arm and the second arm from the locked configuration to the compressed configuration; and an unlocked position in which the first retention member does not block relative motion of the first arm and the second arm from the locked configuration to the compressed configuration.

13. The system of claim 8, wherein:

the implant comprises an implant width measured at a widest portion of the implant; and the implant inserter further comprises:

a first distance between the first arm and the third arm in the locked configuration; and a second distance between the first arm and the third arm in the compressed configuration;

wherein the first distance and the second distance are less than or equal to the implant width.

14. A system for inserting an implant into an intervertebral space, the system comprising:

an implant comprising an implant width measured at a widest portion of the implant; and an implant inserter, comprising:

a first arm;

a second arm;

a third arm; and a fourth arm;

wherein:

the first arm and the second arm are moveable, relative to each other, and the third arm and the fourth arm are moveable, relative to each other, between:

a locked configuration in which the first arm is spaced apart from the second arm and the third arm is spaced apart from the fourth arm, such that the first arm, the second arm, the third arm, and the fourth arm are locked in place relative to the implant; and a compressed configuration, in which the first arm is less spaced apart from the second arm and the third arm is less spaced apart from the fourth arm, such that the first arm, the second arm, the third arm, and the fourth arm are withdrawable from the implant; and the implant inserter further comprises:

a first distance between the first arm and the third arm in the locked configuration; and a second distance between the first arm and the third arm in the compressed configuration;

wherein:

the first distance and the second distance are less than or equal to the implant width;

in the locked configuration, the implant is secured to the implant inserter; and in the compressed configuration, the implant is removable from the implant inserter.

15. The system of claim 14, the implant further comprising:

a first recess configured to receive a first protruding feature on the first arm;

a second recess configured to receive a second protruding feature on the second arm;

a third recess configured to receive a third protruding feature on the third arm; and a fourth recess configured to receive a fourth protruding feature on the fourth arm.

16. The system of claim 14, wherein:

the first arm and the second arm are further moveable, relative to each other, along a first direction between the locked configuration and the compressed configuration;

the third arm and the fourth arm are further moveable, relative to each other, along the first direction between the locked configuration and the compressed configuration; and the first direction is transverse to a second direction along which the first arm, the second arm, the third arm, and the fourth arm are withdrawable from the implant in the compressed configuration.

17. The system of claim 16, wherein:

the implant further comprises:

a first recess extending parallel to the first direction to receive a first protruding feature on the first arm;

a second recess extending parallel to the first direction to receive a second protruding feature on the second arm;

a third recess extending parallel to the first direction to receive a third protruding feature on the third arm; and a fourth recess extending parallel to the first direction to receive a fourth protruding feature on the second arm.

18. The system of claim 14, wherein the implant inserter further comprises:

a first retention member; and
a second retention member,
wherein the first retention member and the second retention member are moveable between:
a locked position in which the first retention member blocks relative motion of the first arm and the second arm from the locked configuration to the compressed configuration; and
an unlocked position in which the first retention member does not block relative motion of the first arm and the second arm from the locked configuration to the compressed configuration.

19. The system of claim 14, wherein a first distance between the first arm and the third arm and a second distance between the second arm and the fourth arm are generally equal in the locked configuration as in the compressed configuration.

20. The system of claim 14, wherein the first arm and the second arm are moveable relative to each other only in a first plane, and the third arm and the fourth arm are moveable relative to each other only in a second plane that is parallel to and spaced apart from the first plane.

21. The system of claim 14, wherein the implant is configured to apply a force to the first arm, the second arm, the third arm, and the fourth arm to transition from the locked configuration to the compressed configuration.

22. A system for inserting an implant into an intervertebral space, the system comprising:
an implant; and
an implant inserter, comprising:
a first arm;
a second arm; and
a first retention member;
wherein the first arm and the second arm are moveable, relative to each other, between:
a locked configuration in which the first arm and the second arm are spaced apart such that the first arm and the second arm are locked in place relative to the implant and the implant is secured to the implant inserter through interlocking engagement of the first arm and the implant; and
a compressed configuration, in which the first arm and the second arm are less spaced apart such that the first arm and the second arm are withdrawable from the implant;
wherein the first retention member is moveable between:
a locked position in which the first retention member blocks relative motion of the first arm and the second arm from the locked configuration to the compressed configuration; and
an unlocked position in which the first retention member does not block relative motion of the first arm and the second arm from the locked configuration to the compressed configuration,
wherein the implant comprises a first recess configured to receive a first protruding feature on the first arm, and a second recess configured to receive a second protruding feature on the second arm.

23. The system of claim 22, wherein the implant inserter further comprises:
a third arm;
a fourth arm; and
a second retention member;
wherein the third arm and the fourth arm are moveable, relative to each other, between:
a locked configuration in which the third arm and the fourth arm are spaced apart such that the third arm and the fourth arm are locked in place relative to the implant; and
a compressed configuration, in which the third arm and the fourth arm are less spaced apart such that the third arm and the fourth arm are withdrawable from the implant;
wherein the second retention member is moveable between:
a locked position in which the second retention member blocks relative motion of the third arm and the fourth arm from the locked configuration to the compressed configuration; and
an unlocked position in which the second retention member does not block relative motion of the third arm and the fourth arm from the locked configuration to the compressed configuration.

24. The system of claim 23, wherein:
the implant further comprises an implant width measured at a widest portion of the implant; and
the implant inserter further comprises:
a first distance between the first arm and the third arm in the locked configuration; and
a second distance between the first arm and the third arm in the compressed configuration;
wherein the first distance and the second distance are less than or equal to the implant width.

25. A system for inserting an implant into an intervertebral space, the system comprising:
an implant; and
an implant inserter, comprising:
a first arm;
a second arm;
a third arm;
a fourth arm;
a first retention member; and
a second retention member; and
the implant configured to be removably coupled with the implant inserter;
wherein the first arm and the second arm are moveable, relative to each other, and the third arm and the fourth arm are moveable, relative to each other, between:
a locked configuration in which the first arm is spaced apart from the second arm and the third arm is spaced apart from the fourth arm, such that the first arm, the second arm, the third arm, and the fourth arm are locked in place relative to the implant; and
a compressed configuration, in which the first arm is less spaced apart from the second arm and the third arm is less spaced apart from the fourth arm, such that the first arm, the second arm, the third arm, and the fourth arm are withdrawable from the implant;
wherein the implant is configured to apply a force to the first arm, the second arm, the third arm, and the fourth arm to transition from the locked configuration to the compressed configuration,
wherein the implant comprises:
a first recess configured to receive a first protruding feature on the first arm;
a second recess configured to receive a second protruding feature on the second arm;
a third recess configured to receive a third protruding feature on the third arm; and
a fourth recess configured to receive a fourth protruding feature on the fourth arm.

26. The system of claim 25, wherein:

the first arm and the second arm are further moveable, relative to each other, along a first direction between the locked configuration and the compressed configuration;

the third arm and the fourth arm are further moveable, relative to each other, along the first direction between the locked configuration and the compressed configuration; and the first direction is transverse to a second direction along which the first arm, the second arm, the third arm, and the fourth arm are withdrawable from the implant in the compressed configuration.

27. The system of claim 26, further comprising the implant;

wherein the implant comprises:

a first recess extending parallel to the first direction to receive a first protruding feature on the first arm;

a second recess extending parallel to the first direction to receive a second protruding feature on the second arm;

a third recess extending parallel to the first direction to receive a third protruding feature on the third arm; and a fourth recess extending parallel to the first direction to receive a fourth protruding feature on the second arm.

* * * * *